United States Patent
Puranen et al.

(10) Patent No.: US 8,748,149 B2
(45) Date of Patent: Jun. 10, 2014

(54) USE OF PECTINOLYTIC ENZYMES FOR THE TREATMENT OF FRUIT AND VEGETABLE MASH AND ENZYME SEQUENCES THEREFOR

(75) Inventors: Terhi Puranen, Nurmijärvi (FI); Bernhard Seiboth, Vienna (AT); Klaudija Milos, Altrip (DE); Wilfried Theiss, Rossdorf (DE); Jarno Kallio, Järvenpää (FI); Christian Kubicek, Vienna (AT); Jari Vehmaanperä, Klaukkala (FI)

(73) Assignee: AB Enzymes GmbH, Darmstadt (DE)

( * ) Notice: Subject to any disclaimer, the term of this patent is extended or adjusted under 35 U.S.C. 154(b) by 504 days.

(21) Appl. No.: 12/994,075

(22) PCT Filed: May 22, 2009

(86) PCT No.: PCT/EP2009/003638
§ 371 (c)(1),
(2), (4) Date: Nov. 22, 2010

(87) PCT Pub. No.: WO2009/141156
PCT Pub. Date: Nov. 26, 2009

(65) Prior Publication Data
US 2011/0086133 A1    Apr. 14, 2011

(30) Foreign Application Priority Data
May 23, 2008   (DE) .......................... 10 2008 024 778

(51) Int. Cl.
*C12N 9/24* (2006.01)
*C12N 1/15* (2006.01)
*C12N 1/19* (2006.01)

(52) U.S. Cl.
USPC .................... 435/200; 435/254.1; 435/254.2; 435/254.21

(58) Field of Classification Search
CPC .......... C12N 9/24; C12N 15/63; C07H 21/04
USPC ............... 435/77, 200, 254.11, 254.2, 254.21
See application file for complete search history.

(56) References Cited

U.S. PATENT DOCUMENTS

| 2005/0069934 A1 | 3/2005 | Berka et al. |
| 2011/0086408 A1* | 4/2011 | Power et al. .................. 435/197 |

FOREIGN PATENT DOCUMENTS

| EP | 0 696 319 A1 | 2/1996 |
| EP | 0 696 319 B1 | 2/1996 |
| WO | 94/14952 A1 | 7/1994 |
| WO | 94/14966 A1 | 7/1994 |
| WO | 03/012071 A2 | 2/2003 |

OTHER PUBLICATIONS

Database UniProt (Online), Mar. 3, 2009, SubName: Full=Endopolygalacturonase, Database Accession No. B7ZEN3, XP-002540071.
S.A. Mohamed et al., "New polygalacturonases from *Trichoderma reesei*: characterization and their specificities to partially methylated and acetylated pectins", Carbohydrate Research, vol. 338, pp. 515-524 (2003).

\* cited by examiner

*Primary Examiner* — Tekchand Saidha
(74) *Attorney, Agent, or Firm* — Edwards Wildman Palmer LLP; Peter F. Corless

(57) ABSTRACT

The invention relates to the use of one or more pectinolytic enzyme(s) for the treatment of fruit or vegetable mash as well as a process for enzymatic treatment of fruit or vegetable mash comprising the step of adding one or more pectinolytic enzyme(s), wherein at least one pectinolytic enzyme is obtainable from *Trichoderma reesei*, as well as to a process for the preparation of a fruit or vegetable juice comprising the process for enzymatic treatment of fruit or vegetable mash. Moreover, the invention discloses recombinant DNA molecules encoding a polypeptide having endo-polygalacturonase activity, a polypeptide having exo-polygalacturonase activity, a polypeptide having exo-rhamnogalacturonase activity and a polypeptide having xylogalacturonase activity.

9 Claims, 8 Drawing Sheets

Figure 1:
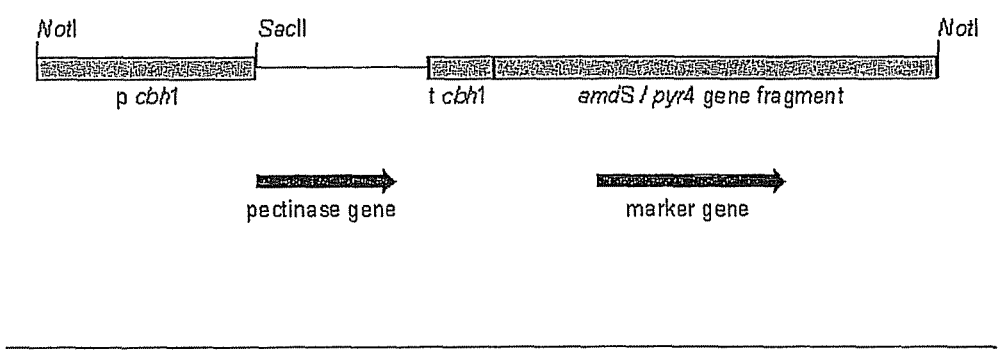

2A
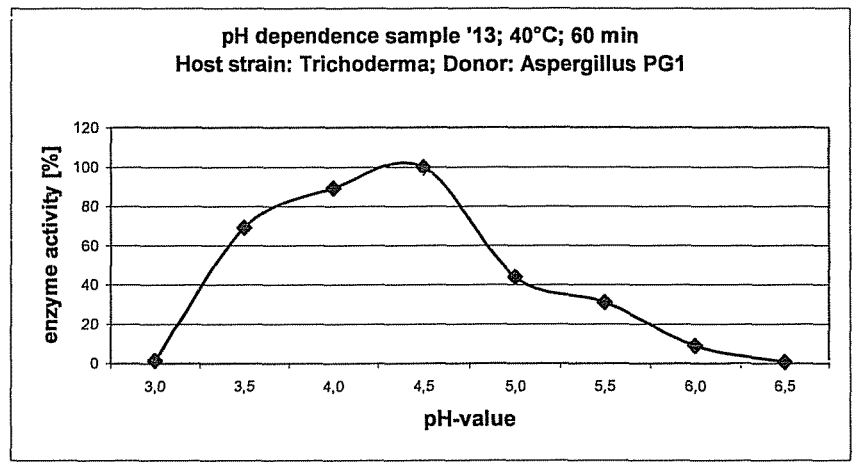
2B
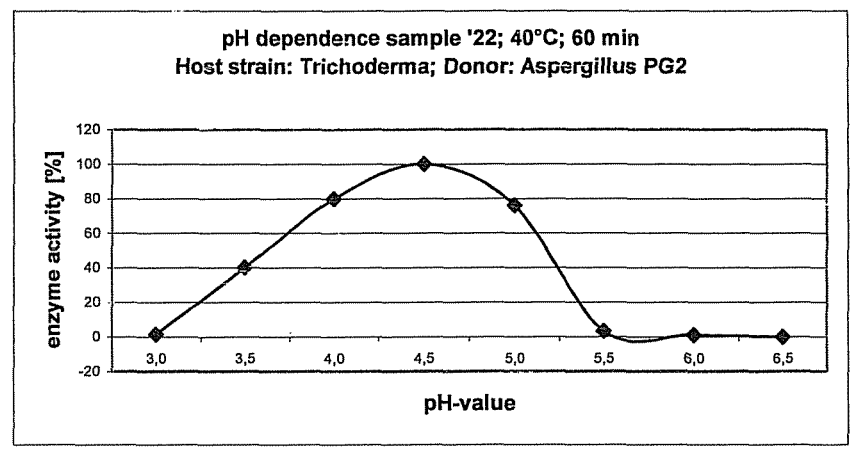
2C
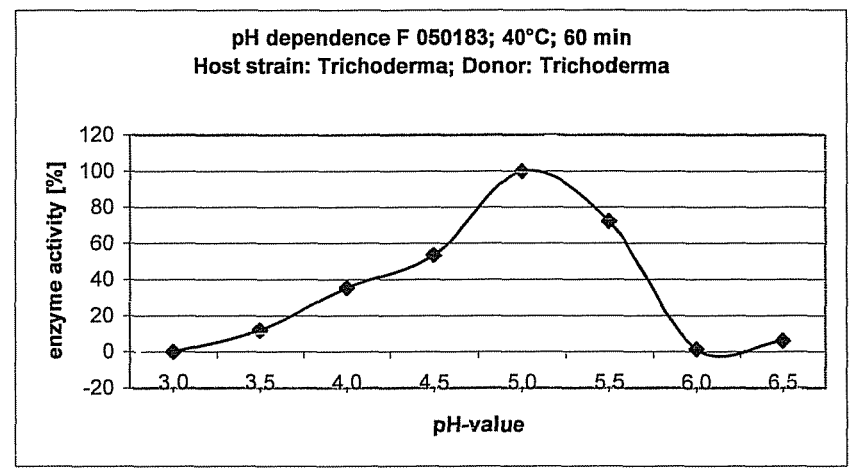
Figures 2A - C

2D
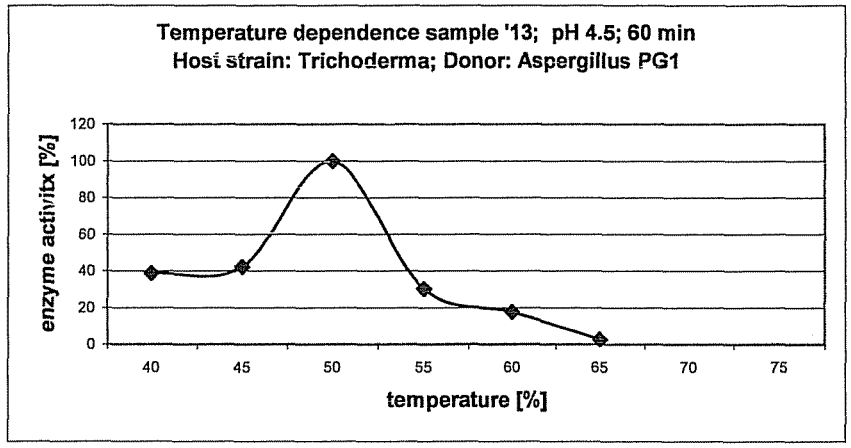
2E
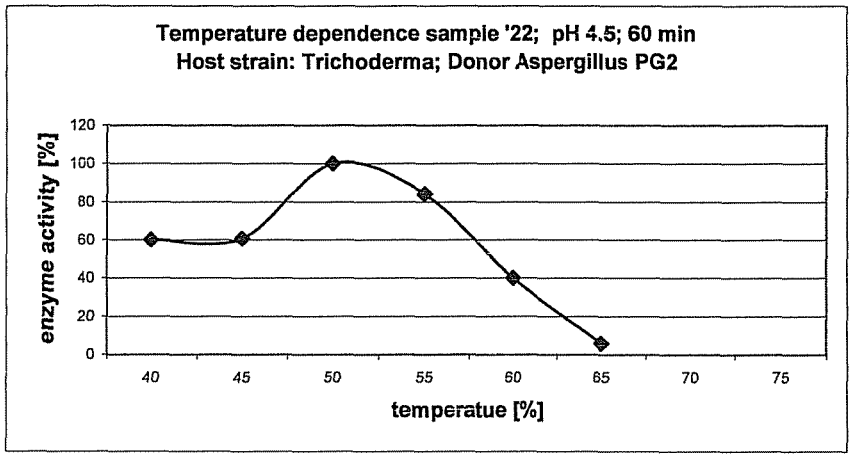
2F
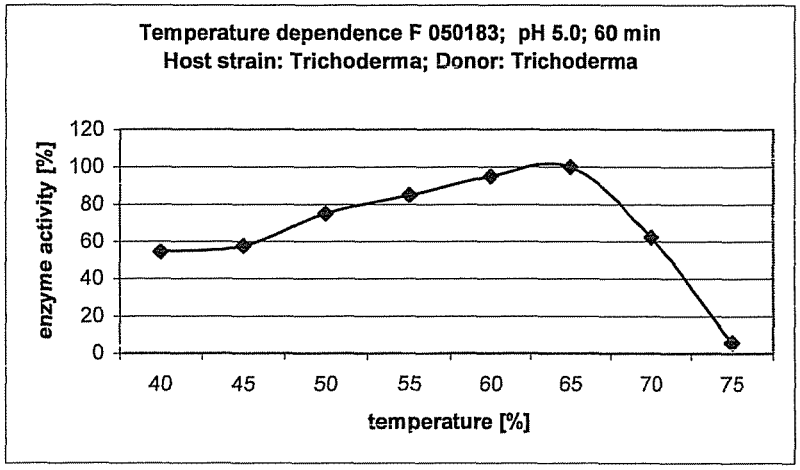
Figures 2D - F

Figures 4A + B

USE OF PECTINOLYTIC ENZYMES FOR THE TREATMENT OF FRUIT AND VEGETABLE MASH AND ENZYME SEQUENCES THEREFOR

The present invention relates to the use of pectinolytic enzymes or polypeptides having pectinolytic activity for the treatment of fruit or vegetable mash. The invention further relates to the use of pectinolytic enzymes for the preparation of fruit or vegetable juice. At least one of the enzymes is obtainable from *Trichoderma reesei*. Moreover, the invention relates to polypeptide sequences having pectinolytic activity suitable in the treatment of fruit or vegetable mash as well as to polynucleotides encoding said polypeptide sequences. Particularly, the invention relates to the use of a polygalacturonase from *Trichoderma reesei* in the treatment of fruit or vegetable mash, particularly apple mash, as well as to the use of said enzyme for the preparation of fruit or vegetable juice, in particular apple juice.

Pectin polymers are important constituents of plant cell walls. Pectin is the major structural polysaccharide of fruit or vegetable lamella and cell walls. The texture of fruit or vegetable depends on the quantity and properties of pectin. Generally, unripe fruit contains insoluble protopectin, whereas ripe fruit contains more soluble pectin. Pectin is a heteropolysaccharide with a backbone composed of alternating homogalacturonans (smooth regions) and rhamnogalacturonans (hairy regions). The smooth regions are linear polymers of 1,4-linked α-D-galacturonic acid. The galacturonic acid residues can be methylesterified on the carboxyl group.

A fruit contains pectinolytic enzymes, which participate in the natural maceration process during and after ripening. Industrial pectinases are used in processing fruit and vegetable in feed and food. In industrial processes enzymes are used, e.g. in fruit or vegetable processing, in order to hydrolyse pectin and to increase the juice when pressing fruit or vegetable, to lower the viscosity to be able to concentrate cloudy juices or to degrade pectin completely in order to clarify juices and to concentrate them.

Fruit and vegetable juices, especially juice made from apples, can be produced either by a pressing operation or by liquefaction processes. Both processes are supported by the use of pectinolytic enzymes. Basically, the whole fruits are milled and treated with pectinolytic enzymes prior to pressing to loosen cell walls and to promote the free run of the juice. After pressing, the juice usually is heated, which inactivates all the enzymes in the juices. Afterwards the juice is transferred to clarification tanks where additional enzyme is added to the juice to depectinize and hydrolyse starch prior to filtration. Then the enzymes are inactivated during the later pasteurisation of the juice or in the evaporator during concentration. For example, in the production of apple juice a certain structure of the mash is required for a good pressing result. Pectinases that provoke the degradation or maceration of so-called insoluble pectins are unfavourable, since they increase solids in the juice. If the structure is completely destroyed, the so-called apple sauce effect is attained and the juice is very cloudy after pressing. Pectinases act preliminarily on soluble pectins and, thus, result in a lower viscosity of the juice assay and a very easy run off. In the preparation of purees macerative properties are preferred.

In the prior art fruit mashes/fruit juices have already been prepared by using pectinolytic enzymes, containing smooth and hairy region pectinases. "Smooth region" pectinases comprise pectin esterases (or pectin methyl-esterases), polygalacturonases and pectin lyases (or pectin trans-eliminases). "Hairy region" pectinases comprise mainly endo-arabanases, arabinofuranosidases, rhamnogalacturonases, arabino-galactanases, among others. Both enzyme categories are present in standard pectinase preparations derived from *Aspergillus niger*. In the prior art process the pectinase is added during crushing of the apples in order to achieve suitable distribution of the enzyme in the mash as stirring is not recommended. After a holding time of 30-120 minutes, the mash is pressed by horizontal or belt press systems. The obtained juice is sieved in order to separate coarse particles. Afterwards the juice is pasteurized or essence-stripped in a vacuum evaporator. After re-cooling to about 48-52° C., the juice treatment takes place in order to depectinize and degradate the starch. This treatment takes about 1-2 hrs followed by a filtration process, i.e. ultrafiltration.

Pectinase preparations (pectinase compositions) of the prior art consisting of "smooth region" and "hairy region" pectinases are not suitable for such described press processes, as they liquefy the mash and cause high amounts of solids in the juice. The exclusive application of a specific polygalacturonase in combination with a high pectin esterase supplies much better press results, i.e. shorter press cycles, higher press yields and lower solids in the juice. Furthermore the juice contains less or no residual pectin, which improves subsequent depectinisation and filtering.

At the processing of clear juices, a $2^{nd}$ processing step called "depectinisation" is required, in which usually both "smooth region" and "hairy region" pectinases are used. In principle, it is necessary to degrade all present high molecular substances (mainly pectins, starch, etc.) in order to achieve an optimized ultrafiltration process. The pectinases used in the prior art processes are not satisfactory as regards their performance at higher temperatures or the quality of the obtained juice.

Currently pectinases that are active at higher temperatures (>60° C.) are not available. Moreover, pectinases used for the mash treatment yielding directly clear juice after pressing without residual pectin are not satisfactorily available at present. Pectinolytic enzymes are known from the prior art. *Aspergillus* pectinases are, for example, disclosed in WO 94/14952 and WO 94/14966. Carbohydrate Research 338 (2003), 515-524, describes the isolation and characterisation of two *Trichoderma reesei* (ATCC 26920) polygalacturonase isoforms belonging to the glycosyl hydrolase family 28. The enzyme is characterised in terms of its pH and temperature properties. A particular use of said polygalacturonases is not described.

Consequently, there has been a need in the prior art for pectinolytic enzymes being suitable for the treatment of fruit or vegetable mash in terms of easier handling as regards the temperature properties and the conduct of the process.

Accordingly, it is an object of the present invention to provide an improved process for the preparation of fruit or vegetable juice. In particular, it is an object of the present invention to provide an improved process for the preparation of fruit or vegetable mash. The method of the invention is to lead to a better yield and quality in terms of the finally obtained juice. Moreover, the process of the invention should be practicable over a wide range of temperatures and should also lead to good results when the process is carried out at high temperatures. The process of the invention is to improve the extractability or degradability and, thus, the press capacity of the mash. It is to lead to juices with a low content of residual pectins after pressing, i.e. the clarity of the obtained juices is to be improved and, thus, avoids laborious filtrations. The process of the invention should be suitable for different fruits.

A further object of the invention is to provide genes encoding pectinolytic enzymes as well as to provide the sequences of polypeptides having pectinolytic activity being suitable in the above-mentioned process. In particular, the sequences of the invention are to encode pectinolytic enzymes having a broad application range and leading to improvements in the process of the treatment of mash and the preparation of fruit or vegetable juice.

It has now surprisingly been found that pectinases from *Trichoderma reesei* show excellent performance in the treatment of fruit or vegetable mash and specifically in the treatment of a mash from fruits that contain soluble or low esterified pectin. In particular, it has been found that the *Trichoderma reesei* polygalacturonase (PGA1) shows excellent performance in apple mash treatments. It has surprisingly been found that *Trichoderma reesei* polygalacturonase (PGA1) can be used as the sole enzyme for the treatment of a mash from fruits that contain soluble or low esterified pectin and the process can favourably be conducted at elevated temperatures. It has further been found that *Trichoderma reesei* polygalacturonase PGA1 can favourably be used in combination with further pectinolytic enzymes, like pectin methylesterases, polygalacturonases, pectin lyases, pectate lyases, arabinofuranosidases, endo-arabanases or rhamnogalacturonases to improve the treatment of fruit mash even from fruits having high esterified or insoluble pectin, whereby the process has to be conducted at a temperature that is compatible to the enzymes used.

The invention relates to the use of one or more pectinolytic enzymes for the treatment of fruit or vegetable mash, wherein at least one pectinolytic enzyme is obtainable from *Trichoderma reesei*. In particular, the invention relates to the use of a polygalacturonase from *Trichoderma reesei* in the treatment of apple mash. Moreover, the invention relates to the process for enzymatic treatment of fruit or vegetable mash comprising the step of adding one or more pectinolytic enzyme(s) as well as to a process for the preparation of a fruit or vegetable juice comprising said process for enzymatic treatment of fruit or vegetable mash, wherein at least one pectinolytic enzyme is obtainable from *Trichoderma reesei*. In particular, the invention relates to a process for enzymatic treatment of apple mash, whereby a polygalacturonase from *Trichoderma reesei* having SEQ ID NO: 2 is used.

The invention, moreover, relates to a recombinant DNA molecule that upon expression in a prokaryotic or eukaryotic host cell encodes a polypeptide having endo-polygalacturonase activity, said recombinant DNA molecule comprising a DNA sequence selected from a) DNA sequences having or comprising SEQ ID NO: 1 (pga1), b) DNA sequences hybridizing with the DNA sequences of a) under stringent conditions, c) DNA sequences having a degree of identity of 70% to 98% to the sequences of a) or d) DNA sequences being related to the sequences of a), b) or c) due to the degeneracy of the genetic code.

The invention, moreover, relates to a recombinant DNA molecule that upon expression in a prokaryotic or eukaryotic host cell encodes a polypeptide having exo-polygalacturonase activity. The recombinant DNA molecule comprising a DNA sequence selected from a) DNA sequences having or comprising SEQ ID NO: 3 (pgx1), b) DNA sequences hybridizing with the DNA sequences of a) under stringent conditions, c) DNA sequences having a degree of identity of 60% to 98% to the sequences of a) or d) DNA sequences being related to the sequences of a), b) or c) due to the degeneracy of the genetic code.

Furthermore, the invention relates to a recombinant DNA molecule that upon expression in a prokaryotic or eukaryotic host cell encodes a polypeptide having exo-rhamnogalacturonase activity, the recombinant DNA molecule comprising a DNA sequence selected from a) DNA sequences having or comprising SEQ ID NO: 5 (rgx1), b) DNA sequences hybridizing with the DNA sequences of a) under stringent conditions, c) DNA sequences having a degree of identity of 60% to 98% to the sequences of a) or d) DNA sequences being related to the sequences of a), b) or c) due to the degeneracy of the genetic code.

The invention also relates to a recombinant DNA molecule that upon expression in a prokaryotic or eukaryotic host cell encodes a polypeptide having xylogalacturonase activity, the recombinant DNA molecule comprising a DNA sequence selected from a) DNA sequences having or comprising SEQ ID NO: 7 (xga1), b) DNA sequences hybridizing with the DNA sequences of a) under stringent conditions, c) DNA sequences having a degree of identity of 60% to 98% to the sequences of a) or d) DNA sequences being related to the sequences of a), b) or c) due to the degeneracy of the genetic code.

The invention also relates to a polypeptide having pectinolytic activity and comprising an amino acid sequence selected from: a) a polypeptide comprising an amino acid sequence having at least 77% identity, preferably at least 80% identity, more preferred at least 85% identity, still more preferred at least 90% identity, still more preferred at least 95% identity and still more preferred at least 98% identity to the sequence of the PGAI polypeptide (SEQ ID NO: 2); (b) a variant of a) comprising a fragment having pectinolytic activity; and c) a fragment of a) or b) having pectinolytic activity.

The invention further relates to a polypeptide having exo-polygalacturonase, exo-rhamnogalacturonase or xylogalacturonase activity and comprising an amino acid sequence selected from a) a polypeptide comprising an amino acid sequence having at least 60% identity, preferably at least 70% identity, more preferred at least 80% identity, still more preferred at least 90% identity and still more preferred at least 95% identity to the sequence of the polypeptides SEQ ID NO: 4, SEQ ID NO: 6 or SEQ ID NO: 8, and b) a variant of a).

For the purpose of the present invention the term "pectinolytic enzyme" is to comprise pectinases, pectin esterases (or pectin methyl-esterases), polygalacturonases, pectin lyases (or pectin trans-eliminases), pectate lyases (or pectate trans-eliminases), arabinofuranosidases, endo-arabanases or rhamnogalacturonases.

When preparing a fruit or vegetable mash according to the present invention, the fruit or vegetable in question is first crushed, then the mash is treated with the pectinolytic enzyme of the present invention, then the mash is pressed and the thus obtained juice is optionally pasteurised and optionally further treated with (the) pectinolytic enzyme(s) and/or with other enzymes suitable for the conduct of the process. In this connection the temperature characteristics of the further enzymes to be used should be taken into account as regards the overall conduct of the process at higher temperatures.

The pectinolytic enzyme is added directly during or after crushing and in amounts usual in the art. The preferable application is to use a pectinase preparation consisting of 50.000-100.000 PGU/mg in a 1-5% solution. The recommended dosage of the enzyme is 50-100 g/t of fruits. The recommended reaction temperature is 10-30° C., the reaction time is 30-120 minutes. The average pH of the mash is 3.2-3.6.

The pectinolytic enzyme can be added in any form that is convenient and compatible with the conduct of the process.

The pectinolytic enzyme is preferably added as concentrated or diluted liquid solution.

Preferably, the pectinolytic enzyme is a pectinolytic enzyme having one of the sequences SEQ ID NO: 2, SEQ ID NO: 4, SEQ ID NO: 6 and SEQ ID NO: 8. Most preferable is the polygalacturonase from *Trichoderma reesei* having SEQ ID NO: 2.

The process described above is suitable for the treatment of any fruit or vegetable mash. Suitable fruits are selected from apples, pears, grapes, white grapes, red grapes, berries and plums. The process is suitable both for fruits that are processed at cold temperatures (p.ex. 10-30° C.) and for fruits that are processed at high temperatures (p.ex. 50° C.). Suitable vegetables are selected from carrots and tomatoes. Other processable material may include coffee or cacao beans and pepper.

Most favourable results are obtained when the fruit mash is an apple mash and the enzyme used is polygalacturonase from *Trichoderma reesei*. Particularly favourable results are obtained when the fruit mash is a mash from fruits that contain low esterified and soluble pectin like strawberries or plums. It has been found that in this case a juice in high yield and high quality can be obtained by use of *Trichoderma* PGA1 as single enzyme. In the case of fruits that contain highly esterified and/or insoluble pectin the use of additional pectinolytic enzymes in the process of preparing a corresponding juice may be necessary.

The invention also relates to the DNA and protein sequences of novel pectinolytic enzymes from *Trichoderma reesei*. Those sequences are an endo-polygalacturonase (pga1), an exo-polygalacturonase (pgx1), an exo-rhamnogalacturonase (rgx1) and a xylogalacturonase (xga1). The sequences are given in the enclosed sequence listing as SEQ ID NO: 1 to SEQ ID NO: 8.

The invention also comprises variants and derivatives of said DNA sequences as long as they encode a polypeptide having the claimed activity. Specifically comprised by the invention are DNA sequences that hybridise to the respective sequence under stringent conditions. Examples of stringent conditions are hybridisation at 65° C., 18 h in dextransulfate solution (GenescreenPlus, Dupont), washing of the filters for 30 min, first with 6×SSC, twice with 2×SSC, three times with 3×SSC, with 0.1% SDS and after that 0.2×SSC at 65° C. (membrane transfer and detection method, Amersham).

Preferably, the invention relates to a polynucleotide having a degree of identity of at least 70%, preferably at least 80%, more preferred at least 85%, still more preferred at least 90%, still more preferred at least 95%, still more preferred at least 98% to the sequence of pga1 (SEQ ID NO: 1).

Preferably, the invention relates to a polynucleotide having a degree of identity of at least 60%, preferably at least 70%, more preferred at least 75%, still more preferred at least 80%, still more preferred at least 85%, still more preferred at least 90%, still more preferred at least 95% and still more preferred at least 98% to one of the sequences selected from pgx1 (SEQ ID NO: 3), rgx1 (SEQ ID NO: 5) and xga1 (SEQ ID NO: 7).

Furthermore, the invention relates to DNA sequences that are related to the sequences according to the present invention due to the degeneracy of the genetic code as well as all their allelic variants. The degeneracy of the genetic code may result from a natural degeneracy or from a especially selected use of the codon. Naturally occurring allelic variants can be identified by using well-known techniques of molecular biology, such as the polymerase chain reaction (PCR), or hybridisation techniques.

A DNA sequence encoding a polypeptide according to the present invention may be used to transform any host cell, such as cells of fungi, yeast, bacteria, plants or mammals.

The degree of identity is preferably determined by detecting the number of residues of the shorter sequence taking part in the comparison and having an "appropriate" counterpart in the other sequence. In this respect homology is defined as degree of identity. For the purposes of the present invention identity is preferably determined in the usual way by using standard algorithms. According to the present invention, only the cDNAs of the respective proteins are used for the comparison, and similar, preferably identical, sequence counterparts were determined as homologous sequences by means of known computer programmes. An example of such a programme is Clone Manager Suite, a programme that includes the programme part Align Part and is sold by Scientific & Educational Software, Durham, N.C., USA. Under the option "local alignment" this programme conducts a comparison of two DNA sequences as defined above by using either the FastScan-MaxScore method or the Needleman-Wunsch method and by retaining the default values. According to the present invention, the programme version "Clone Manager 7 Align Plus 5" including the functions "Compare Two Sequences/Global/Compare DNA sequences" was especially used for determining the degree of identity. In this case algorithms available from the following sources were used: Hirschberg, D. S. (1975) A linear space algorithm for computing longest common subsequences, Commun. Assoc. Comput. Mach. 18:341-343; Myers, E. W. and W. Miller. (1988) Optimal alignments in linear space, CABIOS 4:1, 11-17; Chao, K-M, W. R. Pearson and W. Miller. (1992) Aligning two sequences Within a specified diagonal band, CA-BIOS 8:5, 481-487.

Expression of the cloned gene sequence(s) results in the production of the desired protein, or in the production of a fragment of this protein. This expression can take place in a continuous manner in the transformed cells, or in a controlled manner.

Fragments are understood to be parts of polypeptide or nucleic acid molecules long enough to have the desired enzymatic properties or to code for the described pectinolytic polypeptides or a biologically active fragment thereof. Preferably, fragement sequences are the respective mature polypeptide sequences without a signal sequence.

The invention also relates to polypeptides having sequences with a degree of identity of at least 60%, preferably at least 70%, more preferred at least 80%, still more preferred at least 90% and most preferred at least 95% with the above polypeptide sequences SEQ ID NOs: 2, 4, 6 or 8 or fragments thereof or parts of it as long as the polypeptide retains the respective pectinolytic activity. Preferably, the invention relates to a polypeptide having a degree of identity of at least 77%, preferably at least 80%, more preferred at least 85%, still more preferred at least 90%, still more preferred at least 95% and still more preferred at least 98% to the sequence of the the PGA1 polypeptide (SEQ ID NO: 2).

As used in the present context the term "identity" of polypeptides refers to the global identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite; Rice et al., 2000) program package, version 3.0.0, with the following parameters: EMBLOSUM62, Gap penalty 10.0, Extend penalty 0.5. The algorithm is desribed in Needleman and Wunsch (1970) Journal of Molecular Biology 48, 443-453.

The terms "protein", "peptide" and "polypeptide" are to be rendered interchangeable. A polypeptide or enzyme with endo-polygalacturonase, exo-polygalacturonase, exo-rhamnogalacturonase or xylogalacturonase activity denotes an enzyme having said activity according to established assays in the art. The invention also includes variants of the claimed enzymes as long as they retain their original activity. A variant according to the present invention includes variants of polypeptides that are derived by deletion or addition of one or more amino acid(s) to the N-terminal and/or C-terminal end of the native protein; deletion or addition of one or more amino acid(s) to one or more sites in the native protein; or substitution of one or more amino acid(s) to one or more sites in the enzyme. The production of such variants is generally well known to persons skilled in the art. Variants of amino acid sequences of polypeptides can, for example, be produced by mutations in the DNA. Methods of mutagenesis and changes in the nucleotide sequence are well known to persons skilled in the art (cf., for example, Kunkel, Proc. Natl. Acad. Sci. USA, 82:488 (1985), Kunkel et al., Methods in Enzymol., 154:367 (1987), U.S. Pat. No. 4,873,192, Walker and Gaastra, eds., Techniques in Molecular Biology, Mac Millan Publishing Company, New York (1983)). References on appropriate substitutions of amino acids, which do not negatively influence the biological activity of the protein of note, can be found in the model from Dayhoff et al., Atlas of Protein Sequence and Structure, Natl. Biomed. Res. Found., Washington, D.C. (1978). Conservative substitutions are preferred, such as exchanging one amino acid by another one with similar properties.

This kind of amino acids, which are interchangeable within a group, are listed in the following Table but not limited to it.

| aliphatic | non-polar | G A P M |
| | | I L V F W |
| | polar and uncharged | C S T N Q Y |
| | polar and charged | D E |
| | | K R H |
| aromatic | | H F W Y |

The invention also relates to isolated or essentially purified nucleic acid preparations (compositions) or protein preparations (compositions). In this respect an isolated and purified polynucleotide/polypeptide or its segment refers to a polynucleotide or polypeptide or its segment that occurs isolated from its natural environment. An isolated segment of a polynucleic acid or polypeptide may occur in a purified form or may occur in a non-native environment, such as in a transgenic host cell.

The present invention also relates to expression cassettes, which can be used to introduce an open reading frame, which encodes a pectinolytic enzyme according to the invention, into a host cell. They preferably include a promoter with a transcription start region, which is linked to the open reading frame of the desired DNA sequence. Such an expression cassette may include a variety of restriction cleavage sites for the insertion of the open reading frame and/or other DNAs, e.g. a transcription regulator region and/or selectable marker genes. In the 5'→3' direction of the transcription, the expression cassette includes a promoter with a transcription and translation start region, the DNA desired sequence and a translation and transcription termination regions. The expression cassette of such is functional in a microbial cell. The termination region may be native to the promoter or the DNA in question or may be derived from any different source.

The term "open reading frame" (ORF) refers to the amino acid sequence that is coded between the translation start and stop codons of an encoding sequence. The terms "start codon" and "stop codon" refer to a unit of three contiguous nucleotides (codons) in a coding sequence, which specify the chain start and chain stop of the protein synthesis (mRNA translation).

In connection with a nucleic acid "functional linkage" refers to a compound as a part of the same nucleic acid molecule in an appropriate position and with an appropriate orientation to the transcription start of the molecule. DNA functionally linked to a promoter is under the transcription initiation regulation of the promoter. Coding sequences may be functionally linked to a regulator sequence in sense orientation or antisense orientation. With reference to polypeptides "functional linkage" refers to the connection as a part of the same polypeptide, i.e. by means of peptidyl bonds.

According to the present invention any promoter may be used. Usually, promoter refers to the upstream of the nucleotide sequence in regard to the coding sequence and controls the expression of the coding sequence by recognition of the RNA polymerase and other factors that are necessary for a correct transcription. The promoter used according to the present invention may include a minimal promoter, i.e. a short DNA sequence from a TATA box and other sequences that specify the transcription start site to which regulator elements are bound for the expression.

The promoter according to the present invention may also include a nucleotide sequence that comprises a minimal promoter and regulator elements; this minimal promoter may check the expression of a coding sequence or functional RNA.

The invention also relates to vectors including the DNA according to the present invention. These vectors comprise any plasmid, cosmid, phage and other vector in a double-stranded or single-stranded, linear or circular form; these vectors themselves might be transmitted or mobilised and can transform a prokaryotic or eukaryotic host via integration into the cellular genome or they occur extrachromosomally (e.g. autonomously replicating plasmids with a replication origin).

The construction of vectors that can be used according to the present invention is, known to the skilled person due to the aforementioned disclosure (cf., e.g., Sambrook et al., Molecular Cloning: A Laboratory manual ($2^{nd}$ edition, Coldspring Harbor Laboratory Press, Plainview, N.Y. (1989). The expression cassette according to the present invention may include one or more restriction enzyme cleavage site(s) to inserting the nucleotide sequence, which encodes a pectinolytic enzyme, under the regulation of a regulator sequence. The expression cassette may also include a termination signal functionally linked to the polynucleotide as well as regulator sequences, which are necessary for the proper translation of the polynucleotide.

Selecting an appropriate expression vector depends on the host cells. Expression vectors of yeast or fungi may include a replication origin, an appropriate promoter and enhancer as well as any necessary ribosome binding site, polyadenylation site, splice donor and acceptor site, transcription termination sequence and non-transcribed 5'-flanking sequences.

Examples of appropriate host cells are: fungal cells of the genus *Aspergillus, Rhizopus, Trichoderma, Hypocrea, Neurospora, Mucor, Penicillium, Chrysosporium, Myceliophthora, Fusarium* etc., such as yeasts of the genera *Kluyveromyces, Saccharomyces, Schizosaccharomyces, Trichosporon, Schwanniomyces, Hansenula, Pichia* and others of this category. Appropriate host systems are, for example, fungi like *Aspergilli*, e.g. *Aspergillus niger* (ATCC 9142) or *Aspergillus ficuum* (NRLL 3135) or *Trichoderma* (e.g. *Trichoderma reesei* QM6a and derivatives thereof) and yeasts like *Saccharomyces*, e.g. *Saccharomyces cerevisiae* or *Pichia*, such as *Pichia pastoris* or *Hansenula*, e.g. *H. poly*-

*morpha* (DSMZ 70277). Such micro-organisms can be obtained from recognised depositories, e.g. American Type Culture Collection (ATCC), Centraalbureau voor Schimmelcultures (CBS) [Central Office for Mildew Cultures] or Deutsche Sammlung für Mikroorganismen und Zellkulturen GmbH (DSMZ) [German Collection of Micro-Organisms and Cell Cultures] or any other depository.

Additionally to the use of a special promoter, other types of elements can influence the expression of cloned genes. It was shown in particular that introns have the potential for enhancing the gene expression.

The expression cassette may also include further elements, such as elements that can be regulated by endogenous or exogenous elements like zinc finger proteins, including naturally occurring zinc finger proteins or chimeric zinc finger proteins.

The expression cassette used according to the present invention can also include enhancer elements or upstream promoter elements.

Vectors used according to the present invention can be constructed in such a way that they include an enhancer element. Thus, the constructs according to the present invention include the gene of interest together with a 3'-DNA sequence, which acts as a signal to terminate the transcription and to allow for the polyadenylation of the thus obtained mRNA. Any signal sequence that allows secretion from the selected host organism possible can be used. The most preferred signal sequences for the secretion from filamentous fungi are the glucoamylase (glaA) or phytase signal sequence from *Aspergillus niger*, the TAKA-amylase signal sequence from *A. oryzae*, and the cellobiohydrolase I signal sequence from *T. reesei*, or signal sequences derived from these. Alternatively, the signal sequence of the desired protein could be used.

It is also possible to use a special leader sequence, since the DNA sequence between the transcription start site and the start of the encoding sequence, i.e. the non-translated leader sequence, may influence the gene expression. Preferred leader sequences include sequences that control the optimal expression of the attached gene, i.e. they have a preferred consensus leader sequence that increases or preserves the mRNA stability and avoids an inappropriate translation initiation. The choice of such sequences is well known to the person skilled in the art.

As soon as the expression cassette or DNA sequence according to the present invention is obtained, it can be inserted into vectors by means of known methods to overexpress the encoded polypeptide in appropriate host systems. However, DNA sequences themselves may also be used to transform appropriate host systems of the present invention to attain an overexpression of the encoded polypeptide.

As soon as a DNA sequence according to the present invention is expressed in an appropriate host cell in a suitable medium, the encoded enzyme can be concentrated and/or isolated by known methods either from the medium if the enzyme is secreted into the medium or from the host organism if the enzyme occurs intracellularly, or in periplasmatic space. Known methods for separating the biomass and solids of the culture medium followed by methods for concentrating the enzyme can be used for the production of concentrated enzymatic solutions or as preparation for the dehydration of the enzyme.

The invention also relates to preparations that include the polypeptide according to the invention. In general these preparations are liquid or dry. Liquid preparations preferably include the enzyme in a purified or enriched form. However, adjuvants such as a stabiliser with glycerol, sorbitol or propylene glycol, borate, additives such as salts, sugar, preservatives, means for adjusting the pH value, etc. can be added. Typical liquid preparations are aqueous or oily suspensions.

As used in the present context, the "enzyme preparation" refers to any enzyme product which contains at least one pectinolytic enzyme of the invention. Thus, such an enzyme preparation may be a spent culture medium or filtrate. Spent culture medium means the culture medium of the host comprising the produced enzymes. Preferably, the host cells are separated from said medium after the production. If desired, such preparations may be spray-dried, granulated or lyophilized or the the preparations may be otherwise concentrated and/or stabilized for storage. If required, a desired enzyme may be further purified in accordance with conventional methods, such as extraction, precipitation, chromatography, electrophoresis, or the like.

However, it is an advantage of the invention that the culture medium with or without host cells may be utilized as an enzyme preparation as such without further purification, because the pectinolytic enzyme of the invention can be secreted into the culture medium and displays activity in the ambient conditions of the spent culture medium. Such enzyme preparations are very economical to provide and use, because isolation of a specific enzyme from the culture medium is unnecessary.

In addition to the pectinolytic enzyme, the enzyme preparations may comprise one or more other enzymes, which may be, for example, other cellulases, amylases, lipases, proteases, hemicellulases, xylanases, pectinases and/or oxidases such as laccases and peroxidases.

In addition to the pectinolytic enzyme, the enzyme preparation may contain additives such as stabilizers, buffers, preservatives, surfactants and/or culture medium components. Preferred additives are such which are commonly used in enzyme preparations intended for the application where the enzyme preparation is used.

Dry preparations can include freeze-dried, spray-dried, instantized, granulated or extruded preparations, which can solely comprise the enzyme, or have additives like starch, dextrin, sugar, flour, protein or oil.

The enclosed Figures are to illustrate the invention in more detail:

FIG. 1. Schematic picture of the expression cassettes used in the transformation of *Trichoderma reesei* protoplasts for overproducing the pectinase proteins. The pectinase genes were under the control of *T. reesei* cbh1 (cel7A) promoter (p cbh1) and the termination of the transcription was ensured by using *T. reesei* cbh1 terminator sequence (t cbh1). Either the amdS gene or pyr4 gene was included as a transformation selection marker.

FIGS. 2A-C) pH dependencies of the state-of-the-art *Aspergillus* PG1 (2A), *Aspergillus* PG2 (2B) and the overproduced crude *Trichoderma* PGA1 preparation of the invention (2C) determined at various pH-values (40° C., 60 min).

FIGS. 2D-F) Temperature dependency of the state-of-the-art *Aspergillus* PG1 (2D), *Aspergillus* PG2 (2E) and the overproduced crude *Trichoderma* PGA1 preparation of the invention (2F) determined at various temperatures (2D and 2E pH 4.5, 2F pH 5.0, 60 min).

Figure 3:
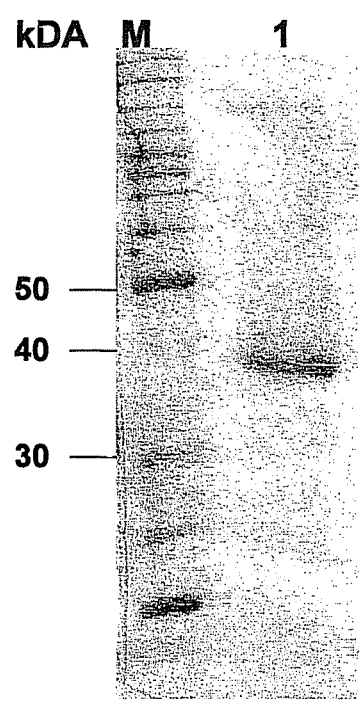

FIG. 3. SDS-PAGE analysis of the *Trichoderma reesei* PGA1 protein. MW: molecular weight marker, lane 1: culture supernatant of transformant overproducing *Trichoderma* PGA1 as described in Example 3. Protein bands were visualised by staining with Coomassie Brilliant Blue. The size of the *Trichoderma* PGA1 is about 38 kDa.

Figure 4A:
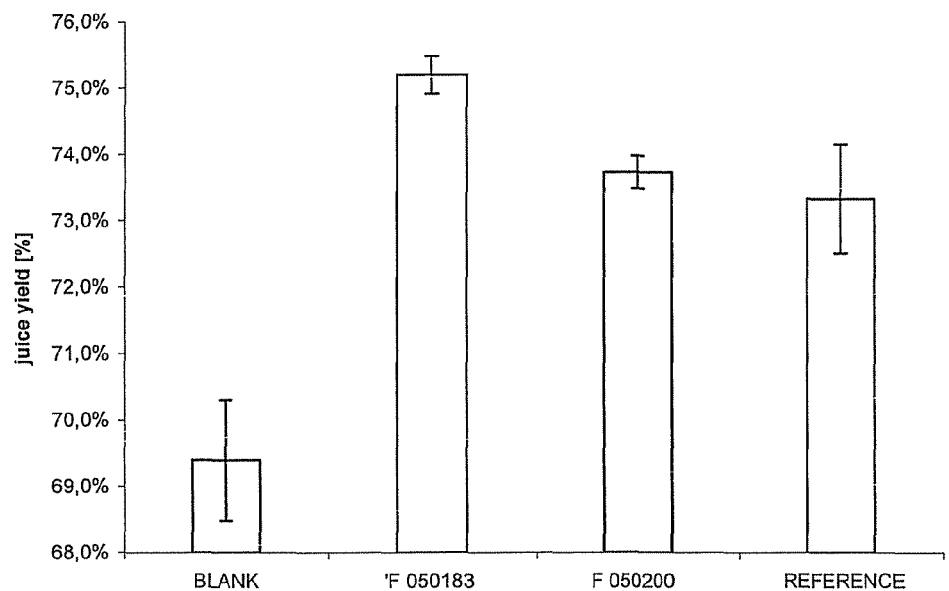
Figure 4B:
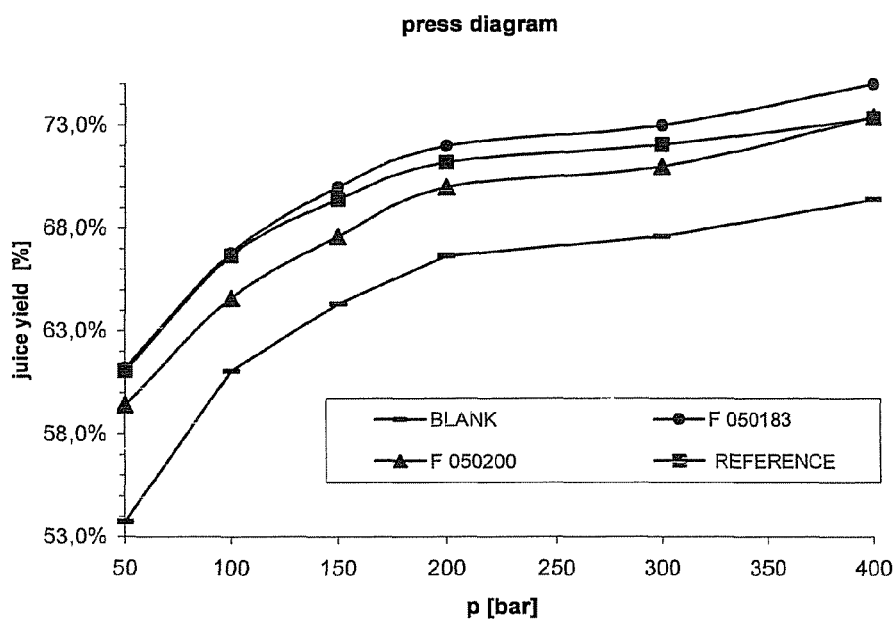

FIG. 4. A) Juice yield after pressing the enzyme treated apple mash preparations. Dosage of 100 ppm of a mixture containing 50 000 PG units/mg of either the *Trichoderma* PGA1s (F050183 and F050200) or the state-of-the-art *Aspergillus* PG1 (REFERENCE), all supplied with 2000 PE units/g of *A. niger* pectin methyl esterase, was used in the experiment. In one of the mash trials no enzyme was added (BLANK). Enzyme incubation time was 60 min at 25° C.

B) Press diagram showing the juice yield after each pressure step.

Figure 5:
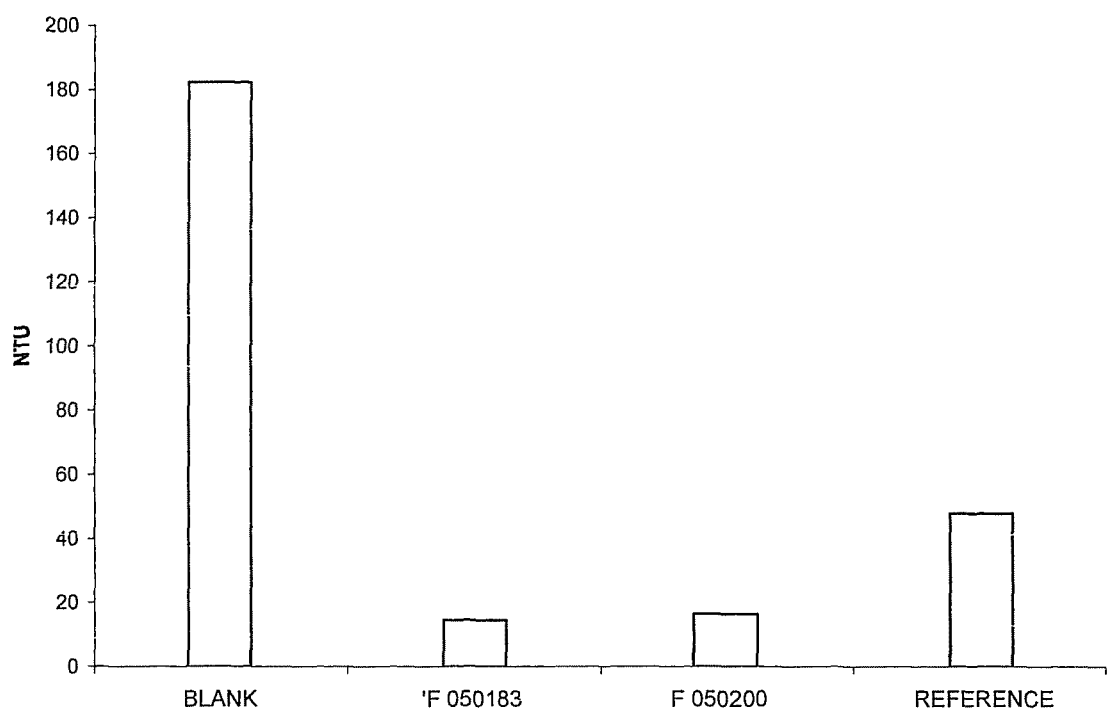

FIG. 5. Turbidity (measured as NTU) of the juice after enzyme treatment and pressing. Dosage of 100 ppm of a mixture containing 50 000 PG units/mg of either the *Trichoderma* PGA1s (F050183 and F050200) or the state-of-the-art *Aspergillus* PG1 (REFERENCE), all supplied with 2000 PE units/g of *A. niger* pectin methyl esterase, was used in the experiment. In one of the mash trials no enzyme was added (BLANK). Enzyme incubation time was 60 min at 25° C.

Figure 6:
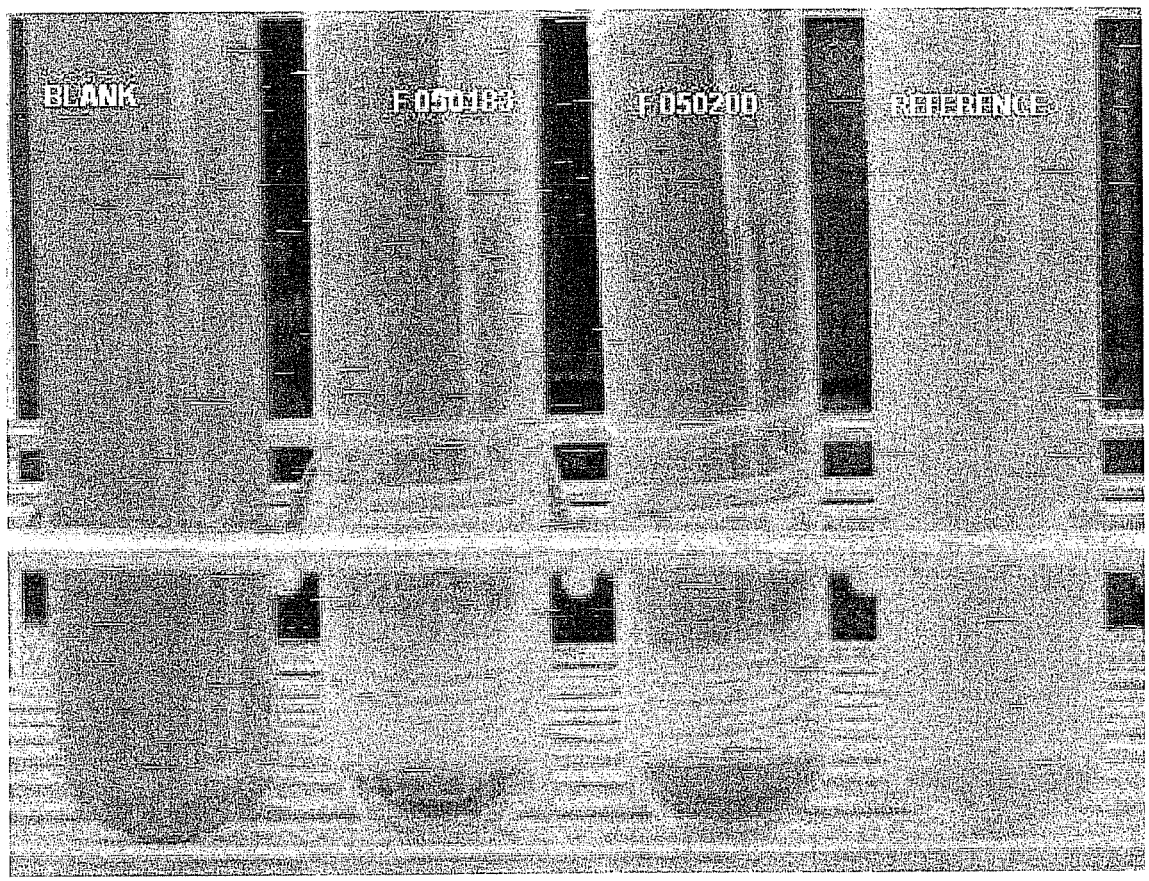

FIG. 6. A photo of the sample juices after the enzyme treatment and pressing. Samples from left to right: Blank (no enzyme), F050183, F0510200 and state of art *Aspergillus* PG1 as a reference.

Figure 7:
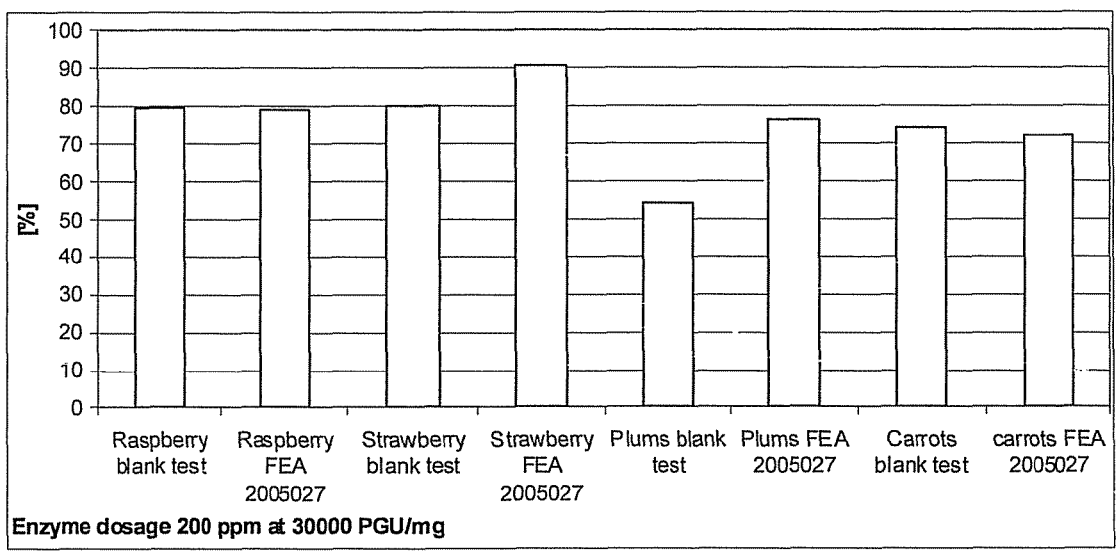

FIG. 7. Yield (%) of the juice obtained from pressings of mashes of different fruits/vegetables after treatment with *Trichoderma reesei* PGA1.

The *E. coli* strain including the plasmid pALK1958 (RF 6249) was deposited at the Deutsche Sammlung von Mikroorganismen und Zellkulturen GmbH (DSMZ), Mascheroder Weg 1 b, D-38124 Braunschweig, Germany on 19 Jul. 2006 and assigned accession number DSM18450. The pALK1958 carries the *Trichoderma* pga1 gene (Table 2) on a 1690 bp SacII-XhoI fragment (including 305 bp of the gene 3'-region) cloned into similarly cut pBluescript II SK+-vector.

The following non-limiting Examples are intended to illustrate the subject-matter of the present invention in detail.

EXAMPLE 1

Genome-Wide Screening of *T. reesei* Pectinolytic Enzymes

Standard molecular biology methods were used in the isolation and enzyme treatments of DNA (plasmids, DNA fragments), in *E. coli* transformations, etc. The basic methods used are described in the standard molecular biology handbooks, e.g. Sambrook et al. (1989). Molecular cloning, a laboratory manual. Cold Spring Harbor Laboratory, New York, USA and Sambrook and Russell (2001). Molecular cloning, a laboratory manual. Cold Spring Harbor Laboratory, New York, USA.

The *Trichoderma reesei* (the anamorph of *Hypocrea jecorina*) genome database (http://gsphere.lanl.gov/trire1/trire1.home.html) was searched with the sequences of various *Aspergillus* pectinases (Table 1) by using the tBlastn program (Altschul et al., 1990. Basic local alignment search tool. J. Mol. Biol. 215:403-410).

Only search with *A. niger* endo-polygalacturonases, *A. tubingensis* exo-polygalacturonases, *A. niger* putative exo-rhamnogalacturonases, and *A. tubingensis* endo-xylogalacturonase produced hits with significant similarity (lower than e-20 over at least 80% of its length), resulting in the identification of four different open reading frames (Table 2). The complete coding regions of these sequences were obtained from http://gsphere.lanl.gov/trire1/trire1.home.html.

TABLE 1

*Aspergillus* Pectinase Gene Sequences Used in the Mining of the *T. reesei* Genome Database.

| Enzyme name | Genes | Accession No. |
|---|---|---|
| *A. niger* endo-polygalacturonases | pgaA | CAB72125 |
| | pgaB | CAB72126 |
| | pgaC | CAA45707 |
| | pgaD | CAB72931 |
| | pgaE | CAA74744 |
| | pgaI | CAA41693 |
| | pgaII | CAA41694 |
| *A. niger* pectin lyases | pelA | CAA43130 |
| | pelB | CAA46521 |
| | pelC | AAW03313 |
| | pelD | AAA32701 |
| *A. niger* pectate lyase | plyA | CAC33162 |
| *A. tubingensis* exo-polygalacturonase | pgaX | CAA68128 |
| *A. tubingensis* (endo)-xylogalacturonase | xghA | CAC07733 |
| *A. niger* rhamnogalacturonases | rhgA | CAA63911 |
| | rhgB | CAA63912 |
| *A. niger* exo-rhamnogalacturonases | rgxA | ABD61566 |
| | rgxB | ABD61567 |
| | rgxC | ABD61568 |
| *A. aculeatus* rhamnogalacturonan lyase | rhgB | 1NKG_A |
| *A. aculeatus* pectin methyl-esterase | pme1 | AAB42153 |
| *A. oryzae* pectin methyl-esterase | pmeA | BAA75474 |
| *A. tubingensis* pectin methyl-esterase | pmeA | P17872 |
| *A. aculeatus* rhamnogalacturonan acetyl-esterase | rha1 | CAA61858 |
| *A. niger* rhamnogalacturonan acetyl-esterase | rgaeA | CAC41360 |

TABLE 2

Putative pectinase encoding genes identified from the *T. reesei* genome database.

| Gene | Gene model/ ProtID | Scaffold: Region (bp) | Identity (%) |
|---|---|---|---|
| pga1 | fgenesh5_pg.C_scaffold_1000682/ 103049 | 1: 2495262-2496642 | *A. fumigatus* polygalacturonase EAL91052; 76% identity<br>*A. nidulans* endo-polygalacturonase ABF50893; 74% identity |
| pgx1 | fgenesh5_pg.C_scaffold_33000038/ 112140 | 33: 88035-89368 | *F. oxysporium* exo-polygalacturonase BAE97149; 56% identity<br>*A. nidulans* exo-polygalacturonase ABF50895; 54% identity |
| rgx1 | estExt_fgenesh5_pg.C_150014/ 122780 | 15: 45898-47405 | *A. niger* exo-rhamnogalacturonase ABD61567; 42% identity<br>*A. fumigatus* exo-polygalacturonase EAL86831; 40% identity |

TABLE 2-continued

Putative pectinase encoding genes identified from the *T. reesei* genome database.

| Gene | Gene model/ ProtID | Scaffold: Region (bp) | Identity (%) |
|---|---|---|---|
| xga1 | e_gw1.33.41.1/ 70186 | 33: 90062-91279 | unnamed protein from *A. oryzae* BAE61127; 54% identity *A. fumigatus* exopolygalacturonase XP_747488; 53% identity |

Analysis of the derived protein sequences with InterProScan (http://www.ebi.ac.uk/InterProScan/, Apweiler et al., 2000 Bioinformatics 16(12):1145-50) identified them as members of glycoside hydrolase family 28 (GH28; InterPro acc. no. PF00295). The putative pectinase encoding sequences from *T. reesei* all showed closest homology to enzymes from other fungi involved in pectin degradation (BLASTP search, Altschul et al., 1990. Basic local alignment search tool. J. Mol. Biol. 215: 403-410, Table 2) and were consequently named pga1 (endo-polygalacturonase), pgx1 (exo-polygalacturonase), xga1 (xylogalacturonase) and rgx1 (exo-rhamnogalacturonase). The identification was further verified by phylogenetic approach (Mega 3.1, Kumar et al., 2004 MEGA3: Integrated software for molecular evolutionary genetics analysis and sequence alignment. Briefings in Bioinformatics. 5:150-163). Three "not-endo-polygalacturonase" sections of the phylogenetic tree thereby formed four branches. PGX1 is found in a branch that also contains the already characterized exo-polygalacturonases from *A. niger*, *A. tubingensis* and *Cochliobolus carbonum*. XGA1 is the most similar to a small branch, in which an *A. tubingensis* xylogalacturonan hydrolase is the only characterized enzyme. XGA1 shares less similarity with the other sequences in that branch than these show towards each other, and it is therefore possible that the *T. reesei* enzyme has developed some unique characteristics. The same applies to RGX1, which shows the highest degree of sequence identity to putative exo-rhamnogalacturonases. In the corresponding branch only an enzyme from *A. niger* has been tested with regard to its functionality without determining the exact reaction mechanism (Martens-Uzunova, E. S., Zandleven, J. S., Benen, J. A., Awad, H., Kools, H. J., Beldman, G., Voragen, A. G., Van den Berg, J. A. & Schaap, P. J. (2006) A new group of exo-acting family 28 glycoside hydrolases of *Aspergillus niger* that are involved in pectin degradation, Biochem J. 400, 43-52).

EXAMPLE 2

Cloning of the Identified *T. reesei* Pectinase Genes

The pga1, pgx1, rgx1 and xga1 genes were amplified from *T. reesei* genomic DNA using the GoTaq® system (Promega, USA) with 2 mM MgCl$_2$ and 0.4 µM of sequence specific primers presented in Table 3. The conditions for the PCR reaction were the following: 2 min initial denaturation step at 95° C., followed by 28 cycles of 1 min at 95° C., 45 s annealing at the primer specific temperature (Table 3_TP), 2 min extension at 72° C. and and a final elongation at 72° C. for 5 min. The DNA fragments of the expected sizes were isolated, and were then cloned to pBlueScript II SK+ vector (Stratagene, USA). The inserts were characterized by sequencing.

TABLE 3

The Primers Used to Amplify the *T. reesei* Pectinase Genes. The genomic DNA of *T. reesei* QM9414 was used as a template in the PCR reactions. The name of the plasmid containing the amplified gene fragment is shown.

| Gene | Primer name | 5' -> 3' sequence | $T_m$[a] [° C.] | Plasmid |
|---|---|---|---|---|
| pga1 | Forward: C22000155for SEQ ID NO: 9 Reverse: C22000155rev SEQ ID NO: 10 | GATCCCGCGG CAACATGCTC AAGCTATCAC GATCCTCGAG CATTCTTCAC GGCATTCTAC | 50 | pALK1958 |
| pgx1 | Forward: C42000032fw SEQ ID NO: 11 Reverse: C42000032rv SEQ ID NO: 12 | CAGTCCGCG GCTAAGCAA AGGAGCACG CGTAGGATCCG TAGTAGAGTT TCATTGCATC | 49 | pALK1961 |
| xga1 | Forward: C42000033fw SEQ ID NO: 13 Reverse: C42000033rv SEQ ID NO: 14 | GACTCCGCGGC GACTTCCATC ATGCTCCTTG GATCACC GCGGATG CTTTATG | 51 | pALK1964 |
| rgx1 | Forward: C12000223fw SEQ ID NO: 15 Reverse: C12000223rv SEQ ID NO: 16 | GTACCCGCGGT CGACAGAATGG TGGCGCTATC GTCAGGATCCA GAGCGGTATC AAGCAGTATC | 58 | pALK1970[b]/ pALK1971 |

[a]Annealing temperature used to amplify the *T. reesei* pectinase gene.
[b]The encoding region of the full-length rgx1 gene consisted of two plasmids.

The relevant information on the pectinase genes and the deduced protein sequences are summarized in Table 4 and Table 5, respectively.

TABLE 4

Summary of the *T. reesei* Pectinase Genes.

| Pectinase gene | Length with introns (bp)[a] | Coding region (bp)[b] | No of introns | Lengths of introns (bp) |
|---|---|---|---|---|
| pga1 | 1381 | 1137 | 4 | 64, 59, 59, 59 |
| pgx1 | 1421 | 1311 | 2 | 50, 57 |
| xga1 | 1218 | 1215 | 0 | |
| rgx1 | 1374 | 1371 | 0 | |

[a]The STOP codon is included.
[b]The STOP codon is not included.

TABLE 5

Summary of the deduced *T. reesei* pectinase sequences.

| CBH protein | No of aas | Length of ss NN/HMM[a] | Predicted MW (Da, ss not incl)[b] | Predicted pI (ss not incl) | Putative N-glycosylation sites[c] |
|---|---|---|---|---|---|
| PGAI | 379 | 21/21 | 36 187 | 5.51 | 3 |
| PGXI | 437 | 22/22 | 45 559 | 5.51 | 12 |
| XGAI | 405 | 18/18 | 40 023 | 7.10 | 8 |
| RGXI | 457 | 17/21 | 48 700[d]/48 340 | 4.79 | 7 |

[a]The prediction on the signal sequence (ss) was made using the program SignalP V3.0 (Nielsen et al., 1997. Identification of prokaryotic and eukaryotic signal peptides and prediction of their cleavage sites. Protein Engineering 10: 1-6; Bendtsen et al., 2004. improved prediction of signal peptides: SignalP 3.0. J. Mol. Biol. 340: 783-795); the NN value was obtained using neural networks and HMM value using hidden Markov models.
[b]The predicted signal sequence was not included. The prediction was made using the Compute pI/MW tool at ExPASy server (Gasteiger et al., 2003. ExPASy: the proteiomics server for in-depth protein knowledge and analysis. Nucleic Acids Res. 31: 3784-3788).
[c]The number of sequences N-X-S/T.
[d]The values marked for RGXI are calculated after deleting two possible signal sequences.

The amino acid residues reported to be crucial for catalytic action of the *A. niger* endo-polygalacturonase II (van Santen et al., 1999. 1.68-Å crystal structure of endopolygalacturonase II from *Aspergillus niger* and identification of active site residues by site-directed mutagenesis. J. Biol. Chem. 274:30474-30480; Armand et al., 2000. The active site topology of *Aspergillus niger* endopolygalacturonase II as studied by site-directed mutagenesis. J Biol Chem. 275:691-696) are identified also in *T. reesei* PGAI, PGXI and XGAI. This indicates similar catalytic properties of the *T. reesei* pectinase enzymes to those of *A. niger*. In addition to the active site signature typical for GH28 glycoside hydrolases, PGAI, PGXI and XGAI contain several PbH1 (parallel beta-helix repeats) domains, which are also found in several types of pectinolytic enzymes (Jenkins & Pickersgill, 2001. The architecture of parallel beta-helices and related folds. Prog Biophys Mol Biol. 77:111-175). The findings further confirmed the pectinolytic features of the *T. reesei* genes indicated here.

EXAMPLE 3

Overexpression of the Pectinase Genes in *Trichoderma reesei*

Expression plasmids were constructed for overexpression of the *T. reesei* pectinase genes. The expression plasmids constructed are listed in Table 6. The pga1, pgx1, rgx1 and xga1 genes, including their own signal sequences, were exactly fused to the *T. reesei* cbh1 (cel7A) promoter. The transcription termination was ensured by the *T. reesei* cel7A terminator and the *A. nidulans* amdS marker gene was used for selection of the transformants as described in Paloheimo et al. (2003) High-yield production of a bacterial xylanase in the filamentous fungus *Trichoderma reesei* requires a carrier polypeptide with an intact domain structure. Appl. Env. Microbiol. 69:7073-7082). The linear expression cassettes (FIG. 1), were isolated from the vector backbones after NotI digestion and were transformed into *T. reesei* RF5455 protoplasts (the strain has the genes encoding the two major cellulases CBHI/Cel7A and EGII/Cel5A deleted).

The expression plasmid including endogenous pyr4 marker gene was also constructed for the pga1 gene by ligating 4.7-kb XbaI-HindIII genome fragment of *T. reesei* pyr4 locus after the cel7A terminator in the plasmid. The linear expression cassette was isolated from the vector backbone after NotI digestion and was transformed, into *T. reesei* RF5514 protoplasts (the strain has the genes encoding the two major cellulases CBHI/Cel7A and EGII/Cel5A deleted and strain is also pyrimidine auxotroph).

The transformations were performed as in Penttila et al. (1987, A versatile transformation system for the cellulolytic filamentous fungus *Trichoderma reesei*. Gene 61:155-164) with the modifications described in Karhunen et al. (1993, High frequency one-step gene replacement in *Trichoderma reesei*. I. Endoglucanase I overproduction. Mol. Gen. Genet. 241:515-522), selecting either acetamide as a sole nitrogen source (amdS marker gene) or without uridine supplement (pyr4 marker gene). The transformants were purified on selection plates through single conidia prior to sporulating them on PD.

TABLE 6

The expression cassettes constructed to overproduce pectinase proteins in *Trichoderma reesei*. The overall structure of the expression cassettes was as described in FIG. 1. The cloned pga1, pgx1, rgx1 and xga1 genes were exactly fused to the *T. reesei* cbh1/cel7A promoter.

| T. reesei pectinase | Expression plasmid | Size of the expr. cassette[a] | cbh1 terminator[b] |
|---|---|---|---|
| PGAI | pALK1967 (amdS[c]) | 9.0 kb | 627 bp (AvaII) |
|  | pALK1960 (pyr4[c]) | 10.0 kb |  |
| PGXI | pALK1968 | 9.2 kb | 627 bp (AvaII) |
| RGXI | pALK1974 | 8.8 kb | 627 bp (AvaII) |
| XGAI | pALK1969 | 8.6 kb | 627 bp (AvaII) |

[a]The expression cassette for *T. reesei* transformation was isolated from the vector backbone by using NotI digestion.
[b]The number of the nucleotides from the genomic cbh1 terminator region after the STOP codon. The restriction site at the 3'-end, used in excising the genomic gene fragment, is included in the parenthesis.
[c]Two expression plasmids were constructed for pga1 gene; the pALK1967 plasmid included amdS marker gene for transformant selection, and the pALK1960 included pyr4 marker gene.

The pectinase production of the transformants was analysed from the culture supernatants of the shake flask cultivations (50 ml). The transformants were grown for 7 days in a complex lactose-based cellulase-inducing medium (Joutsjoki et al. 1993. Transformation of *Trichoderma reesei* with the *Hormoconis resinae* glucoamylase P (gamP) gene: production of a heterologous glucoamylase by *Trichoderma reesei*. Curr. Genet. 24:223-228) buffered with 5% $KH_2PO_4$. The polygalacturonase activity was assayed by a viscosimetric method using citrus pectin (Copenhagen pectin X-2955, Denmark) as the substrate, as described in patent EP0388593. One polygacturonase unit (PGU) is defined as the quantity of enzyme which caused 15 $nPas^{-1}$ reduction in viscosity under standard conditions. The genotypes of the chosen transformants were confirmed by using Southern blots in which several genomic digests were included and the respective expression cassette was used as a probe. Overexpression of the PGAI, PGXI, RGXI and XGAI proteins was analyzed by SDS-PAGE with subsequent Coomassive staining. The PGAI protein was noticeable overproduced in *T. reesei* (see FIG. 3), whereas no PGU activity or visible protein overproduction in SDS-PAGE could be detected for the PGXI, RGXI and XGAI transformants that were, however, shown to contain integrated expression cassette. This suggests that very low amount of the PGXI, RGXI and XGAI proteins are produced in *T. reesei*.

The chosen PGAI transformants were cultivated in lab bioreactors at 28° C. in the medium indicated above for 3-4 days with pH control 4.4±0.2 ($NH_3/H_3PO_4$) to obtain material for the application tests. The supernatants were recovered by centrifugation and filtering through Seitz-K 150 and EK filters (Pall SeitzSchenk Filter-systems GmbH, Bad Kreuznach, Germany). Two preparations were produced with identical enzyme profiles (PGA1+++, CBHI−, EGII−). F050183 was produced with RF5514 derived transformant and F050200 with RF5455 derived transformant; the former was selected with the pyr4 marker and the latter with the amdS marker. Thus the former strain carries only homologous DNA.

EXAMPLE 4

Characterization of the *T. reesei* PGAI Enzyme

The crude *T. reesei* PGAI enzyme was characterized in terms of pH optimum and thermal stability.

The pH dependency of the overproduced *T. reesei* PGAI protein (sample F 050183) was determined within a pH range of 3.0-8.0 by preparing the sample buffer by mixing 0.1 M citric acid and 0.2 M $Na_2HPO_4$ (both supplemented with bovine serum albumin (BSA) 100 microgram/ml (Fluka, Cat. #05470) to the desired pH. The activity was assayed at the desired pH with 60 min incubations. FIGS. 2A-C shows the results. The *Aspergillus* enzymes have a pH optimum around 4.5, whereas the *Trichoderma* PGA1 has a slightly more neutral pH optimum at pH 5.0. The *Trichoderma* PGA1 still retains about 70% activity at pH 5.5, at which the *Aspergillus* PG1 has only 30% of the maximal activity left. *Aspergillus* PG2 looses its activity at pH 5.5.

The temperature dependency of the overproduced *Trichoderma* PGAI protein (sample F050183) was determined at pH 5.0 within the range of 40° C.-75° C., and compared to the state-of-the-art *Aspergillus* PG1 and PG2 assayed at their optimal pH 4.5. Surprisingly, the *Trichoderma* PGA1 has a high temperature optimum at about 65° C., and still about 60% of maximal activity at 70° C., whereas the *Aspergillus* enzymes have virtually no activity left at 65° C. (FIGS. 2D-F), and have their optimum around 50° C. (about 15° C. lower than *Trichoderma* PGA1).

Colorimetric Method for PG Activity

For the pH dependency determinations, the assay was carried out at the desired pH of the substrate and the sample buffer at 40° C. for 60 min. For the temperature dependence determinations, the assay was carried out at pH 4.5 for the *Aspergillus* samples ('13 and '22) and pH 5.0 for the *T. reesei* PGA1 sample. Assays were carried out at the desired temperature for 60 min.

Substrate: 0.7% (w/v) potassium pectate (Fluka, Cat #51186). 0.7 g substrate was dissolved in 100 ml hot water. After cooling down to room temperature the pH value was adjusted with acetic acid or sodium hydroxide.

Enzyme solution: The enzymes were diluted in the sample buffer.

PAHBAH-Reagent:

Stock solution (5%) 50 g p-hydroxybenzhydrazide 98% (Fluka Cat #54600) was dissolved in 1000 ml 0.5 M hydrochloride acid.

Working solution: 0.233 g Titriplex III was dissolved in 30 ml 0.5 M sodium hydroxide.

5 ml stock solution was added and filled up to 50 ml with 0.5 M NaOH

Assay volumes:

| | |
|---|---|
| Substrate: | 0.25 ml |
| Enzyme: | 0.1 ml |
| PAHBAH: | 0.65 ml |
| Temperature of colour incubation: | 80° C. |
| Duration of colour incubation: | 15 min |

Sample value:

Substrate was pipetted into a test tube. The reaction was started by adding the enzyme solution. The batch was mixed and incubated at 40° C. for 60 min. After the incubation the reaction was stopped by adding the PAHBAH reagent. For the colour development the samples were incubated for 15 min at 80° C. Thereafter the samples were cooled down in an ice bath for about 5 min and centrifuged (2 min, 13000 rpm). The supernatants were measured photometrically against the blank sample at 412 nm.

Blank:

Substrate and PAHBAH reagent were mixed. After adding the enzyme solution the samples were incubated for 60 min at 40° C. and then for 15 min at 80° C. for colour development. Cooling, centrifugation and photometric measurement were performed as for the sample values.

EXAMPLE 5

Preparation of Apple Juice

The cell-free culture supernatants were tested in apple juice preparation. For this purpose apples (cultivar Golden Delicious) were ground, and 500 g resulting apple mash were used in the experiment. After enzyme addition the mash was incubated 60 min at room temperature (25° C.), and the mash was then pressed with a laboratory press (Hafico). The pressing routine was 2 minutes at 50, 100, 150 and 200 bar, followed by 1 minute at 300 and 400 bar, respectively.

Two *Trichoderma* PGA1 preparations F050183 (*T. reesei* RF5514/pALK1960/#4) and F050200 (*T. reesei* RF5455/pALK1967/#4) were compared to the state-of-the-art product containing *Aspergillus* PGI (reference sample). All three samples were supplemented with *Aspergillus* pectin methylesterase. The polygalacturonase activity was assayed by a viscosimetric method using citrus pectin (Copenhagen pectin X-2955, Denmark) as the substrate, as described above and in patent EP0388593. One polygacturonase unit (PGU) is defined as the quantity of enzyme which caused 15 $nPas^{-1}$ reduction in viscosity under standard conditions. A dosage of 100 ppm of a mixture having 50 000 PG units/mg of either the *Trichoderma* PGA1s or the reference, supplied with 2000 PE units/g (patent EP0388593) was used in the experiment. In one of the mash trials no enzyme was added (blank sample).

Juice yield results (FIG. 4) show that the *Trichoderma* PGA1 is equal or better than the state-of-the-art pectinase preparation. In particular, the turbidity of the *Trichoderma*

PGA1 treated samples was superior, i.e. *Trichoderma* PGA1 treated juices were much more clear and transparent as compared the state-of-the-art *Aspergillus* PG treated juice (FIG. 5). The result is clearly visible (FIG. 6).

Alcohol test for remaining pectin (1+1 volume juice and absolute ethanol) showed after 6 h incubation at 25° C. that the *Trichoderma* PGA1 treated juices contained no residual pectin, whereas the *Aspergillus* PG treated juice contained some residual pectin. In the blank sample considerable amounts of residual pectin were found.

EXAMPLE 6

Test of *Trichoderma* PGA1 in the Preparation of Juice from Different Fruits and Vegetables

*Trichoderma* PGA1 preparation F050183 produced as described in Example 3 was tested in preparation of juice from fruits and vegetables without added pectin methyl esterase.

Strawberries and raspberries were mashed manually with a metal device. Plums and carrots were mechanically crushed with a mincer. Carrots were blanched by micro wave heating at 95° C. 1000 g of mash was placed in a 2000 ml bottle and temperature was adjusted for 20 min before adding enzyme solution. Reaction temperature was 65° C. and reaction time 60 min. Mashing after enzyme reaction was performed by pressing in a Hafico lab press using textile press clothes. The received juice was collected in an Imhoff-flask for settling.

Enzyme and Dosage:

The dosage was based on general recommendation in the art: 200 ppm at 30.000 PGU/mg corresponds with $6*10^6$ PGU/kg carrots, plums, strawberries and raspberries. The activity of enzyme preparation FEA 2005027 was 10300 PGU/mg. The dosage of the enzyme preparation FEA 2005027 per 1000 g carrots was, thus, 0.58 g. The blank test was without an enzyme dosage.

The press diagram used was the following:

1 min filling—2 min 0 bar—2 min 50 bar—2 min 100 bar—2 min 150 bar—2 min 200 bar—1 min 300 bar—1 min 400 bar.

The turbidity measurement (NTU) was carried out with a Dr Lange LTP5 laboratory turbidity photometer at 860 nm. The values are reported as NTU (Neophelometric turbidity Units) on the basis of the DIN 38404 method. The results are shown in the Table 7.

TABLE 7

Test results with juice preparation from raspberries, strawberries, plums and carrots.

| | Juice yield [g] | Juice yield [%] | °Brix | Turbidity NTU | Turbidity 24 h NTU | Sediment [%] |
|---|---|---|---|---|---|---|
| Raspberry blank test | 795 | 79.5 | 9.4 | 58 | 58 | 1.0 |
| Raspberry F050183 | 789 | 78.9 | 9.4 | 50 | 52 | 1.3 |
| Strawberry blank test | 803.9 | 80.39 | 6.3 | 170 | 79 | 12.2 |
| Strawberry F050183 | 906 | 90.6 | 6.3 | 183 | 56 | 14.5 |
| Plums blank test | 543 | 54.3 | 15 | 157 | 142 | 20.0 |
| Plums F050183 | 764 | 76.4 | 17.2 | 143 | 124 | 9.0 |
| Carrots blank test | 742 | 74.2 | 9.5 | 161 | 17.8 | 8.3 |
| Carrots F050183 | 723 | 72.3 | 9.5 | 150 | 72 | 7.7 |

The above table 7 shows that treatment of strawberries and plums with *Trichoderma* PGA1 increased the juice yield and ° Bx (sugar content) without pectin esterase and other pectinolytic activities.

The results are graphically presented in FIG. 7. FIG. 7 shows the yield of a juice obtained from pressing of mashes of different fruits/vegetables after treatment with *Trichoderma reesei* PGA1. The results are shown in comparison to the respective blank values.

Surprisingly, *Trichoderma* PGA1 gave superior result with fruits containing pectin that is low esterified and soluble. Based on the results presented above, it is possible to carry out the treatment of said fruit mash only with the *Trichoderma* PGA1 enzyme at 65° C. in one hour without any additional pectinases. This superior result could not have been expected.

The invention claimed is:

1. An isolated polypeptide having endo-polygalacturonase activity and being encoded by a recombinant DNA molecule, which upon expression in a prokaryotic or eukaryotic host cell encodes said polypeptide having endo-polygalacturonase activity, the recombinant DNA molecule comprising a DNA sequence selected from
   a) DNA sequences comprising SEQ ID NO: 1,
   b) DNA sequences hybridizing with the DNA sequences of a) under stringent conditions which comprise hybridization at 65° C., 18 h in dextransulphate solution, washing of the filters for 30 min, first with 6×SSC, twice with 2×SSC, three times with 3×SSC, with 0.1% SDS and after that 0.2×SSC at 65° C.,
   c) DNA sequences which are at least 95% identical to the sequences of a), or
   d) DNA sequences that are variants of the sequences of a), b or c) due to the degeneracy of the genetic code.

2. An isolated polypeptide having pectinolytic activity and comprising an amino acid sequence selected from:
   a) a polypeptide comprising an amino acid sequence having at least 95% identity to the amino acid sequence of SEQ ID NO: 2;
   b) a variant of a) having pectinolytic activity.

3. A transformed host cell selected from a fungal, a yeast, a bacterial or a mammalian cell comprising at least one recombinant DNA molecule, which upon expression in said host cell encodes a polypeptide having endo-polygalacturonase activity, the recombinant DNA molecule comprising a DNA sequence selected from
   a) DNA sequences comprising SEQ ID NO: 1,
   b) DNA sequences hybridizing with the DNA sequences of a) under stringent conditions which comprise hybridization at 65° C., 18 h in dextransulphate solution, washing of the filters for 30 min, first with 6×SSC, twice with 2×SSC, three times with 3×SSC, with 0.1% SDS and after that 0.2×SSC at 65° C.,
   c) DNA sequences which are at least 95% identical to the sequences of a), or
   d) DNA sequences that are variants of the sequences of a), b or c) due to the degeneracy of the genetic code.

4. The transformed host cell according to claim 3 belonging to the category of *Kluyveromyces, Pichia, Hansenula, Schizosaccharomyces, Aspergillus, Rhizopus, Trichoderma, Hypocrea, Myceliophthora, Chrysosporium, Neurospora, Mucor, Penicillium, Saccharomyces* or *Fusarium*.

5. A preparation comprising the polypeptide according to claim 1, optionally combined with further enzymes and/or excipients.

6. An isolated polypeptide having endo-polygalacturonase activity selected from the group consisting of:
   a) an isolated polypeptide which is encoded by a nucleic acid sequence comprising the nucleotide sequence of SEQ ID NO: 1;
   b) an isolated polypeptide which is encoded by a nucleic acid sequence having at least 95% identity to the nucleotide sequence of SEQ ID NO: 1;
   c) an isolated polypeptide which is encoded by a nucleic acid sequence having at least 98% identity to the nucleotide sequence of SEQ ID NO: 1; and
   d) an isolated polypeptide which is encoded by a nucleic acid sequence consisting of the nucleotide sequence of SEQ ID NO: 1.

7. An isolated polypeptide having endo-polygalacturonase activity selected from the group consisting of:
   a) an isolated polypeptide comprising an amino acid sequence having at least 95% identity to SEQ ID NO: 2; and
   b) an isolated polypeptide comprising an amino acid sequence having at least 98% identity to SEQ ID NO: 2.

8. The isolated polypeptide according to claim 2 comprising an amino acid sequence having at least 95% identity to SEQ ID NO: 2.

9. The isolated polypeptide according to claim 2 comprising an amino acid sequence having at least 98% identity to SEQ ID NO: 2.

* * * * *

SEQUENCE LISTING

<160> NUMBER OF SEQ ID NOS: 16

<210> SEQ ID NO 1
<211> LENGTH: 1381
<212> TYPE: DNA
<213> ORGANISM: Trichoderma reesei
<220> FEATURE:
<223> OTHER INFORMATION: Endo-polygalacturonase (pga 1)
<220> FEATURE:
<221> NAME/KEY: CDS

```
<222> LOCATION: (1)..(252)
<220> FEATURE:
<221> NAME/KEY: CDS
<222> LOCATION: (317)..(739)
<220> FEATURE:
<221> NAME/KEY: CDS
<222> LOCATION: (799)..(928)
<220> FEATURE:
<221> NAME/KEY: CDS
<222> LOCATION: (988)..(1072)
<220> FEATURE:
<221> NAME/KEY: CDS
<222> LOCATION: (1132)..(1378)

<400> SEQUENCE: 1 atg ctc aag cta tca ctt ttt ctc gga gct gtt aca gct tca ctc tgc      48
Met Leu Lys Leu Ser Leu Phe Leu Gly Ala Val Thr Ala Ser Leu Cys
1               5                   10                  15 gtg caa gct cac gct gtg cct ccg ccc acc gtc acc caa gca ccc aag      96
Val Gln Ala His Ala Val Pro Pro Pro Thr Val Thr Gln Ala Pro Lys
                20                  25                  30 ctc gaa gat cga gcc acc acc tgc acc ttc tcc ggc tcc aat ggc gca     144
Leu Glu Asp Arg Ala Thr Thr Cys Thr Phe Ser Gly Ser Asn Gly Ala
            35                  40                  45 tcg tcg gcg agc aag tcg cag aag tcg tgt gcg acc att gtg ctc tcg     192
Ser Ser Ala Ser Lys Ser Gln Lys Ser Cys Ala Thr Ile Val Leu Ser
        50                  55                  60 aac gtt gcc gtt cct tct ggg gtg acg ctc gat ctc agt gat ttg aac     240
Asn Val Ala Val Pro Ser Gly Val Thr Leu Asp Leu Ser Asp Leu Asn
65                  70                  75                  80 gat ggc acg acc gtaagcatcg aaacaatgag ataaatctcc atgagatgtc         292
Asp Gly Thr Thr actgacttgg attgatatat gtag gtc atc ttc gag ggc acc acg act tgg      343
                          Val Ile Phe Glu Gly Thr Thr Thr Trp
                                      85                  90 ggc tac aag gaa tgg tcc ggc cct ctc ctc cag atc gaa ggc aac gac     391
Gly Tyr Lys Glu Trp Ser Gly Pro Leu Leu Gln Ile Glu Gly Asn Asp
        95                  100                 105 atc acc atc caa ggc gcc agc ggt gct gtt ctg aac ccc gat ggc gcc     439
Ile Thr Ile Gln Gly Ala Ser Gly Ala Val Leu Asn Pro Asp Gly Ala
110                 115                 120                 125 cgt tgg tgg gat ggc caa gga ggc aac ggc ggc aag acg aag ccc aag     487
Arg Trp Trp Asp Gly Gln Gly Gly Asn Gly Gly Lys Thr Lys Pro Lys
                130                 135                 140 ttc ttt gct gcc cat gat ctg acc tcc tcg tcc atc acc aac ttg tat     535
Phe Phe Ala Ala His Asp Leu Thr Ser Ser Ser Ile Thr Asn Leu Tyr
            145                 150                 155 atc aag aac acg cca gtt cag gcc gtc agc gtt aat ggt gtg aat ggg     583
Ile Lys Asn Thr Pro Val Gln Ala Val Ser Val Asn Gly Val Asn Gly
        160                 165                 170 ctg act att act ggc atg aca att gac aac agc gct ggt gat agt ggt     631
Leu Thr Ile Thr Gly Met Thr Ile Asp Asn Ser Ala Gly Asp Ser Gly
175                 180                 185 ggc gga cac aat aca gac ggc ttt gat att ggc tct agc tcc aat gtc     679
Gly Gly His Asn Thr Asp Gly Phe Asp Ile Gly Ser Ser Ser Asn Val
190                 195                 200                 205 gtg att agc gga gcc aag gtt tat aac caa gat gac tgc gtt gct gtc     727
Val Ile Ser Gly Ala Lys Val Tyr Asn Gln Asp Asp Cys Val Ala Val
                210                 215                 220 aat tct ggc acg gtaagaaaca gccgaacaaa cagatgaagc ggccggcgca         779
Asn Ser Gly Thr
225 tttgactgac atgatatag aac atc acc ttc act ggg ggt ctt tgc tcc gga    831
                    Asn Ile Thr Phe Thr Gly Gly Leu Cys Ser Gly
```

```
                Asn Ile Thr Phe Thr Gly Gly Leu Cys Ser Gly
                                230                 235 ggc cac ggc ttg tca atc ggc agt gtt ggc ggt cga gac gac aac aca        879
Gly His Gly Leu Ser Ile Gly Ser Val Gly Gly Arg Asp Asp Asn Thr
            240                 245                 250 gtc caa aca gtc aca ttt tcc aac tcg cag gtc act aaa tca gcc aat g      928
Val Gln Thr Val Thr Phe Ser Asn Ser Gln Val Thr Lys Ser Ala Asn
        255                 260                 265 gtcagtatac ttgtcacaca agactttcaa ggttagaggt taatctaacc tgccttcag       987 gc atc cgt atc aag gcc acc gcc ggt aaa act ggc acc atc aag gga        1034
   Gly Ile Arg Ile Lys Ala Thr Ala Gly Lys Thr Gly Thr Ile Lys Gly
       270                 275                 280 gtc acc tac act ggc att act ctg tcc tcg atc aca gg gtaagtcaaa         1082
Val Thr Tyr Thr Gly Ile Thr Leu Ser Ser Ile Thr Gly
285                 290                 295 gatgtaatct ggacgcagtt tctgggcctc ctctgacact tcataacag c tac gga       1138
                                                          Tyr Gly att ctg att gag caa aac tac gac ggt ggt gat ctt cat gga agc cca      1186
Ile Leu Ile Glu Gln Asn Tyr Asp Gly Gly Asp Leu His Gly Ser Pro
300                 305                 310                 315 acg agc ggc atc ccc atc acc aac ctg gtg ctg cag aac atc tct gga      1234
Thr Ser Gly Ile Pro Ile Thr Asn Leu Val Leu Gln Asn Ile Ser Gly
                320                 325                 330 agc aac ggt gtt gta tcc agt gga aac aac att gcc atc gtc tgt ggc      1282
Ser Asn Gly Val Val Ser Ser Gly Asn Asn Ile Ala Ile Val Cys Gly
                    335                 340                 345 agt gga gct tgt tcc aac tgg act tgg agc aat gtc gtc gtc act ggc      1330
Ser Gly Ala Cys Ser Asn Trp Thr Trp Ser Asn Val Val Val Thr Gly
                350                 355                 360 gga aag aag tac ggc agc tgc cag aat gtg ccg agt cct gct act tgt      1378
Gly Lys Lys Tyr Gly Ser Cys Gln Asn Val Pro Ser Pro Ala Thr Cys
365                 370                 375 taa                                                                   1381

<210> SEQ ID NO 2
<211> LENGTH: 379
<212> TYPE: PRT
<213> ORGANISM: Trichoderma reesei
<220> FEATURE:
<223> OTHER INFORMATION: Endo-polygalacturonase (pga 1)

<400> SEQUENCE: 2

Met Leu Lys Leu Ser Leu Phe Leu Gly Ala Val Thr Ala Ser Leu Cys
1               5                   10                  15

Val Gln Ala His Ala Val Pro Pro Thr Val Thr Gln Ala Pro Lys
            20                  25                  30

Leu Glu Asp Arg Ala Thr Thr Cys Thr Phe Ser Gly Ser Asn Gly Ala
        35                  40                  45

Ser Ser Ala Ser Lys Ser Gln Lys Ser Cys Ala Thr Ile Val Leu Ser
    50                  55                  60

Asn Val Ala Val Pro Ser Gly Val Thr Leu Asp Leu Ser Asp Leu Asn
65                  70                  75                  80

Asp Gly Thr Thr Val Ile Phe Glu Gly Thr Thr Thr Trp Gly Tyr Lys
                85                  90                  95

Glu Trp Ser Gly Pro Leu Leu Gln Ile Glu Gly Asn Asp Ile Thr Ile
            100                 105                 110

Gln Gly Ala Ser Gly Ala Val Leu Asn Pro Asp Gly Ala Arg Trp Trp
        115                 120                 125
```

```
Asp Gly Gln Gly Gly Asn Gly Gly Lys Thr Lys Pro Lys Phe Phe Ala
        130                 135                 140

Ala His Asp Leu Thr Ser Ser Ile Thr Asn Leu Tyr Ile Lys Asn
145                 150                 155                 160

Thr Pro Val Gln Ala Val Ser Val Asn Gly Val Asn Gly Leu Thr Ile
                165                 170                 175

Thr Gly Met Thr Ile Asp Asn Ser Ala Gly Asp Ser Gly Gly His
            180                 185                 190

Asn Thr Asp Gly Phe Asp Ile Gly Ser Ser Asn Val Val Ile Ser
        195                 200                 205

Gly Ala Lys Val Tyr Asn Gln Asp Asp Cys Val Ala Val Asn Ser Gly
        210                 215                 220

Thr Asn Ile Thr Phe Thr Gly Gly Leu Cys Ser Gly Gly His Gly Leu
225                 230                 235                 240

Ser Ile Gly Ser Val Gly Gly Arg Asp Asp Asn Thr Val Gln Thr Val
                245                 250                 255

Thr Phe Ser Asn Ser Gln Val Thr Lys Ser Ala Asn Gly Ile Arg Ile
                260                 265                 270

Lys Ala Thr Ala Gly Lys Thr Gly Thr Ile Lys Gly Val Thr Tyr Thr
        275                 280                 285

Gly Ile Thr Leu Ser Ser Ile Thr Gly Tyr Gly Ile Leu Ile Glu Gln
        290                 295                 300

Asn Tyr Asp Gly Gly Asp Leu His Gly Ser Pro Thr Ser Gly Ile Pro
305                 310                 315                 320

Ile Thr Asn Leu Val Leu Gln Asn Ile Ser Gly Ser Asn Gly Val Val
                325                 330                 335

Ser Ser Gly Asn Asn Ile Ala Ile Val Cys Gly Ser Gly Ala Cys Ser
            340                 345                 350

Asn Trp Thr Trp Ser Asn Val Val Thr Gly Gly Lys Lys Tyr Gly
        355                 360                 365

Ser Cys Gln Asn Val Pro Ser Pro Ala Thr Cys
    370                 375
```

<210> SEQ ID NO 3
<211> LENGTH: 1421
<212> TYPE: DNA
<213> ORGANISM: Trichoderma reesei
<220> FEATURE:
<223> OTHER INFORMATION: Exo-polygalacturonase (pgx 1)
<220> FEATURE:
<221> NAME/KEY: CDS
<222> LOCATION: (1)..(576)
<220> FEATURE:
<221> NAME/KEY: CDS
<222> LOCATION: (627)..(1238)
<220> FEATURE:
<221> NAME/KEY: CDS
<222> LOCATION: (1296)..(1418)

<400> SEQUENCE: 3

```
atg aca att ctc agt cgt ctg gca gtc ggc gtg gca tta ttg gcc ttt      48
Met Thr Ile Leu Ser Arg Leu Ala Val Gly Val Ala Leu Leu Ala Phe
1               5                   10                  15 ccg gaa ctc att gat gct cac aga gtt ccc gtt aag aga cca aac ctt      96
Pro Glu Leu Ile Asp Ala His Arg Val Pro Val Lys Arg Pro Asn Leu
            20                  25                  30 caa tgg gga ccc aag tcg cca gga cat gca ttt cct cat tct cct aaa     144
Gln Trp Gly Pro Lys Ser Pro Gly His Ala Phe Pro His Ser Pro Lys
        35                  40                  45 cgc cac aag aca tgc tat gtt ccg agt tgc gga agt aac gac gca cct     192
```

```
                                                  -continued

Arg His Lys Thr Cys Tyr Val Pro Ser Cys Gly Ser Asn Asp Ala Pro
     50              55                  60 gag att ctc aaa gct ttc aag agg tgc aac agg gga ggc act gtg gtt    240
Glu Ile Leu Lys Ala Phe Lys Arg Cys Asn Arg Gly Gly Thr Val Val
 65              70                  75                  80 tta aac gag gag tat gtg att gcc tct cct ctc gat ctc aca ttc ctg    288
Leu Asn Glu Glu Tyr Val Ile Ala Ser Pro Leu Asp Leu Thr Phe Leu
                 85                  90                  95 gag tct gta gat gtg gcc atc aca ggc acc atc aaa ttc acg aac gac    336
Glu Ser Val Asp Val Ala Ile Thr Gly Thr Ile Lys Phe Thr Asn Asp
             100                 105                 110 atc gac ttt tgg gtg gtg aac tca ttc aag tac gac ttc caa aac tcc    384
Ile Asp Phe Trp Val Val Asn Ser Phe Lys Tyr Asp Phe Gln Asn Ser
         115                 120                 125 tct gcc ttc tgg cgc ttt gga gga aaa gat gtc aat atc tac ggt ggg    432
Ser Ala Phe Trp Arg Phe Gly Gly Lys Asp Val Asn Ile Tyr Gly Gly
     130                 135                 140 gga cac ggt ttg att gat gga aat ggc caa gcc tgg tat gat cga ttt    480
Gly His Gly Leu Ile Asp Gly Asn Gly Gln Ala Trp Tyr Asp Arg Phe
145                 150                 155                 160 gca gtc gag cct act cta ctg cgt ccc att ctt ctt gtc ctg gat gga    528
Ala Val Glu Pro Thr Leu Leu Arg Pro Ile Leu Leu Val Leu Asp Gly
                165                 170                 175 ctt gat cgt gga tca gtc aca gga ttg aag atg cga aat tcg ccc gat    576
Leu Asp Arg Gly Ser Val Thr Gly Leu Lys Met Arg Asn Ser Pro Asp
            180                 185                 190 gcaggtatct cttcgcctat tcatctggaa tcgttgctaa tgtggttcag tgg ttt     632
                                                        Trp Phe aat ctc att gcc aat agc agt gac att ctg gtc agc gat atc gac atc    680
Asn Leu Ile Ala Asn Ser Ser Asp Ile Leu Val Ser Asp Ile Asp Ile
195             200                 205                     210 gca gtc aag agt gag agc aag aat ccg gcc aag aat ggc gat gga tgg    728
Ala Val Lys Ser Glu Ser Lys Asn Pro Ala Lys Asn Gly Asp Gly Trp
                215                 220                 225 gac act ttt cga agc gat tca gtc gtt ata caa gat tcc tac gtg aat    776
Asp Thr Phe Arg Ser Asp Ser Val Val Ile Gln Asp Ser Tyr Val Asn
            230                 235                 240 aac agc gat gat tgc gta tct ttc aag ccg aac agc acc aac atc atc    824
Asn Ser Asp Asp Cys Val Ser Phe Lys Pro Asn Ser Thr Asn Ile Ile
        245                 250                 255 gtg cag ggc atg cag tgc aac ggc tct cac ggg atc tca gtc ggc tct    872
Val Gln Gly Met Gln Cys Asn Gly Ser His Gly Ile Ser Val Gly Ser
    260                 265                 270 ctg ggc cag tat ccg gca gag tat gat atc gtc gaa cac gta tat gtc    920
Leu Gly Gln Tyr Pro Ala Glu Tyr Asp Ile Val Glu His Val Tyr Val
275                 280                 285                 290 tac aat atc tcg atg tcc aac gcc agc gac gga gct cgt atc aaa gtg    968
Tyr Asn Ile Ser Met Ser Asn Ala Ser Asp Gly Ala Arg Ile Lys Val
                295                 300                 305 tgg cct ggc act gat act cct ttt gaa ccc ggt ctc tct gga ggt gga    1016
Trp Pro Gly Thr Asp Thr Pro Phe Glu Pro Gly Leu Ser Gly Gly Gly
            310                 315                 320 ggg gcc gga tac gtc aag aac gtc act tac gac acc ttt cac aac aat    1064
Gly Ala Gly Tyr Val Lys Asn Val Thr Tyr Asp Thr Phe His Asn Asn
        325                 330                 335 aac aat gac tgg gct att gag atc aat caa tgc tat ggc cag agt aac    1112
Asn Asn Asp Trp Ala Ile Glu Ile Asn Gln Cys Tyr Gly Gln Ser Asn
    340                 345                 350 cag acg atc tgc gac aag tat cct tcc aat atg acc atc agc gat gtc    1160
Gln Thr Ile Cys Asp Lys Tyr Pro Ser Asn Met Thr Ile Ser Asp Val
```

```
                355                 360                 365                 370
gta ttc aaa aac atg tgg gga aca act tcg aag aag tat gac cct aaa            1208
Val Phe Lys Asn Met Trp Gly Thr Thr Ser Lys Lys Tyr Asp Pro Lys
            375                 380                 385 gtt ggg acc ctg aca tgc tcg tct acg gag gtgagtcgaa tcgtgagagg             1258
Val Gly Thr Leu Thr Cys Ser Ser Thr Glu
        390                 395 cacttgtact actacaacct gacacagagt tctttag aaa agc gtg aat atc gcg           1313
                                        Lys Ser Val Asn Ile Ala
                                                            400 gcg aag aac atc tcg gtg gtt aat ccg agt ggc agg att cct cag tgg           1361
Ala Lys Asn Ile Ser Val Val Asn Pro Ser Gly Arg Ile Pro Gln Trp
        405                 410                 415 att tgc acc aat atg gac gaa agc ctg cta gac ata gat tgt gtc ccg           1409
Ile Cys Thr Asn Met Asp Glu Ser Leu Leu Asp Ile Asp Cys Val Pro
    420                 425                 430 gct acg tcg taa                                                            1421
Ala Thr Ser
435

<210> SEQ ID NO 4
<211> LENGTH: 437
<212> TYPE: PRT
<213> ORGANISM: Trichoderma reesei
<220> FEATURE:
<223> OTHER INFORMATION: Exo-polygalacturonase (pgx 1)

<400> SEQUENCE: 4

Met Thr Ile Leu Ser Arg Leu Ala Val Gly Val Ala Leu Leu Ala Phe
1               5                   10                  15

Pro Glu Leu Ile Asp Ala His Arg Val Pro Val Lys Arg Pro Asn Leu
            20                  25                  30

Gln Trp Gly Pro Lys Ser Pro Gly His Ala Phe Pro His Ser Pro Lys
        35                  40                  45

Arg His Lys Thr Cys Tyr Val Pro Ser Cys Gly Ser Asn Asp Ala Pro
    50                  55                  60

Glu Ile Leu Lys Ala Phe Lys Arg Cys Asn Arg Gly Gly Thr Val Val
65                  70                  75                  80

Leu Asn Glu Glu Tyr Val Ile Ala Ser Pro Leu Asp Leu Thr Phe Leu
                85                  90                  95

Glu Ser Val Asp Val Ala Ile Thr Gly Thr Ile Lys Phe Thr Asn Asp
            100                 105                 110

Ile Asp Phe Trp Val Val Asn Ser Phe Lys Tyr Asp Phe Gln Asn Ser
        115                 120                 125

Ser Ala Phe Trp Arg Phe Gly Gly Lys Asp Val Asn Ile Tyr Gly Gly
    130                 135                 140

Gly His Gly Leu Ile Asp Gly Asn Gly Gln Ala Trp Tyr Asp Arg Phe
145                 150                 155                 160

Ala Val Glu Pro Thr Leu Leu Arg Pro Ile Leu Leu Val Leu Asp Gly
                165                 170                 175

Leu Asp Arg Gly Ser Val Thr Gly Leu Lys Met Arg Asn Ser Pro Asp
            180                 185                 190

Trp Phe Asn Leu Ile Ala Asn Ser Ser Asp Ile Leu Val Ser Asp Ile
        195                 200                 205

Asp Ile Ala Val Lys Ser Glu Ser Lys Asn Pro Ala Lys Asn Gly Asp
    210                 215                 220

Gly Trp Asp Thr Phe Arg Ser Asp Ser Val Val Ile Gln Asp Ser Tyr
225                 230                 235                 240
```

```
Val Asn Asn Ser Asp Asp Cys Val Ser Phe Lys Pro Asn Ser Thr Asn
            245                 250                 255

Ile Ile Val Gln Gly Met Gln Cys Asn Gly Ser His Gly Ile Ser Val
        260                 265                 270

Gly Ser Leu Gly Gln Tyr Pro Ala Glu Tyr Asp Ile Val Glu His Val
        275                 280                 285

Tyr Val Tyr Asn Ile Ser Met Ser Asn Ala Ser Asp Gly Ala Arg Ile
        290                 295                 300

Lys Val Trp Pro Gly Thr Asp Thr Pro Phe Glu Pro Gly Leu Ser Gly
305                 310                 315                 320

Gly Gly Gly Ala Gly Tyr Val Lys Asn Val Thr Tyr Asp Thr Phe His
                325                 330                 335

Asn Asn Asn Asn Asp Trp Ala Ile Glu Ile Asn Gln Cys Tyr Gly Gln
            340                 345                 350

Ser Asn Gln Thr Ile Cys Asp Lys Tyr Pro Ser Asn Met Thr Ile Ser
        355                 360                 365

Asp Val Val Phe Lys Asn Met Trp Gly Thr Thr Ser Lys Lys Tyr Asp
    370                 375                 380

Pro Lys Val Gly Thr Leu Thr Cys Ser Ser Thr Glu Lys Ser Val Asn
385                 390                 395                 400

Ile Ala Ala Lys Asn Ile Ser Val Val Asn Pro Ser Gly Arg Ile Pro
                405                 410                 415

Gln Trp Ile Cys Thr Asn Met Asp Glu Ser Leu Leu Asp Ile Asp Cys
                420                 425                 430

Val Pro Ala Thr Ser
        435

<210> SEQ ID NO 5
<211> LENGTH: 1374
<212> TYPE: DNA
<213> ORGANISM: Trichoderma reesei
<220> FEATURE:
<223> OTHER INFORMATION: Exo-rhamnogalacturonase (rgx 1)
<220> FEATURE:
<221> NAME/KEY: CDS
<222> LOCATION: (1)..(1371)

<400> SEQUENCE: 5 atg gtg gcg cta tcg tcc atc att ctg gcg gca ttg ccc atc gct ctc    48
Met Val Ala Leu Ser Ser Ile Ile Leu Ala Ala Leu Pro Ile Ala Leu
1               5                   10                  15 gca gtg tca tct tcg gcc cct gat ctc atg ggc agg gag gca aat gct    96
Ala Val Ser Ser Ser Ala Pro Asp Leu Met Gly Arg Glu Ala Asn Ala
            20                  25                  30 gct cag acg gaa tcc cat tgg gca aac cac gcg gcg gct caa ggt cgc    144
Ala Gln Thr Glu Ser His Trp Ala Asn His Ala Ala Ala Gln Gly Arg
        35                  40                  45 cat ttc tgc tat gtt cga cct gat gcc gac ggt gat gat gca ccg        192
His Phe Cys Tyr Val Arg Pro Asp Ala Asp Gly Gly Asp Asp Ala Pro
    50                  55                  60 gcc ata atg gat gct ctc aac aac aaa tgc aac tca agg agc ctt gtc    240
Ala Ile Met Asp Ala Leu Asn Asn Lys Cys Asn Ser Arg Ser Leu Val
65                  70                  75                  80 atc ttc cct ggg ccc gtg tac aac atc cag aca aac atg acg acc ttg    288
Ile Phe Pro Gly Pro Val Tyr Asn Ile Gln Thr Asn Met Thr Thr Leu
                85                  90                  95 aac ctg gaa gat gtt gtc att tat caa ttt ggg cgc atg ctc tgg agc    336
Asn Leu Glu Asp Val Val Ile Tyr Gln Phe Gly Arg Met Leu Trp Ser
            100                 105                 110
```

```
acg gac att gac tac tgg ctt tca gta tct atg ccc gtt ggc ttc cag        384
Thr Asp Ile Asp Tyr Trp Leu Ser Val Ser Met Pro Val Gly Phe Gln
        115                 120                 125 aat cag agt acg gtc tgg tac ttt ggg ggc aac aat gtc atc tgg gac        432
Asn Gln Ser Thr Val Trp Tyr Phe Gly Gly Asn Asn Val Ile Trp Asp
130                 135                 140 ggt tgg ggt gtt ggt acg ctt gat ggc aac ggt caa gtc tgg tat gac        480
Gly Trp Gly Val Gly Thr Leu Asp Gly Asn Gly Gln Val Trp Tyr Asp
145                 150                 155                 160 tgg gct agg agt caa gga aac ctg cct cac cga ccg atg aac atc aac        528
Trp Ala Arg Ser Gln Gly Asn Leu Pro His Arg Pro Met Asn Ile Asn
                165                 170                 175 ttg cgc acc ctc acc aac tcc gtc atc cga cgg atg cgc ttc gtc caa        576
Leu Arg Thr Leu Thr Asn Ser Val Ile Arg Arg Met Arg Phe Val Gln
                180                 185                 190 agc cag atg tgg aca atg gcc att acg tac tcc cag cat gtt gag ctg        624
Ser Gln Met Trp Thr Met Ala Ile Thr Tyr Ser Gln His Val Glu Leu
            195                 200                 205 gat gac att tat gtc aac agt act tcg aca agc cag tgg agc acg ctg        672
Asp Asp Ile Tyr Val Asn Ser Thr Ser Thr Ser Gln Trp Ser Thr Leu
        210                 215                 220 aac acg gac ggt tgc gac act atc ttt tca gat agc atc act ttc aga        720
Asn Thr Asp Gly Cys Asp Thr Ile Phe Ser Asp Ser Ile Thr Phe Arg
225                 230                 235                 240 aga tgg acc gtc tcc aac ggc gac gat gcc atc gcc ctc aag atg aac        768
Arg Trp Thr Val Ser Asn Gly Asp Asp Ala Ile Ala Leu Lys Met Asn
                245                 250                 255 tcg agt aac att gct gtg tat gac agc tat ttc gag aat gga cag ggc        816
Ser Ser Asn Ile Ala Val Tyr Asp Ser Tyr Phe Glu Asn Gly Gln Gly
                260                 265                 270 ata gcc atc ggg tcc atg gga caa tac aac ggc cga tac gag tat ctg        864
Ile Ala Ile Gly Ser Met Gly Gln Tyr Asn Gly Arg Tyr Glu Tyr Leu
            275                 280                 285 gaa aac ttt tat gcg aaa aac att act ctc aag aat act gct cat gtc        912
Glu Asn Phe Tyr Ala Lys Asn Ile Thr Leu Lys Asn Thr Ala His Val
        290                 295                 300 tcc tac ctc aag aca tgg gct ggc atc tca aga ggg tac ccc ccc aac        960
Ser Tyr Leu Lys Thr Trp Ala Gly Ile Ser Arg Gly Tyr Pro Pro Asn
305                 310                 315                 320 ggt gga ggt ggc ggt tac ggg gtc gcc cga aac att acc atc gag gac       1008
Gly Gly Gly Gly Gly Tyr Gly Val Ala Arg Asn Ile Thr Ile Glu Asp
                325                 330                 335 gtc aaa ctc att ggc gga cga cag caa ccc ttc ttc gcc tgg cag tgc       1056
Val Lys Leu Ile Gly Gly Arg Gln Gln Pro Phe Phe Ala Trp Gln Cys
                340                 345                 350 gaa aac tac tcc gga tac gcc ggc caa gac tgc gac tct tcc ctg ttc       1104
Glu Asn Tyr Ser Gly Tyr Ala Gly Gln Asp Cys Asp Ser Ser Leu Phe
            355                 360                 365 aag atg gaa gat gtt gcg tgg agg cgg gtc agc gga aca gtg caa tct       1152
Lys Met Glu Asp Val Ala Trp Arg Arg Val Ser Gly Thr Val Gln Ser
        370                 375                 380 gga gtg acg gag gcg gcc tat ttc caa tgc agc gcc gcg gct gga gga       1200
Gly Val Thr Glu Ala Ala Tyr Phe Gln Cys Ser Ala Ala Ala Gly Gly
385                 390                 395                 400 tgc gat gac ttt gag gtg acg ggc ttt gat gtt acc aag gag ggc act       1248
Cys Asp Asp Phe Glu Val Thr Gly Phe Asp Val Thr Lys Glu Gly Thr
                405                 410                 415 gac gaa ctt ctg gct ata tgg gac tgc ttc aac gta aac aat ccc gta       1296
Asp Glu Leu Leu Ala Ile Trp Asp Cys Phe Asn Val Asn Asn Pro Val
                420                 425                 430
```

```
ggc ttt acc tgt acc gag tca caa gcc cag aaa atg agc tca gac gtg    1344
Gly Phe Thr Cys Thr Glu Ser Gln Ala Gln Lys Met Ser Ser Asp Val
        435                 440                 445 acc ggc ggc cat ggc tcc aac aac aag tag                            1374
Thr Gly Gly His Gly Ser Asn Asn Lys
    450                 455
```

<210> SEQ ID NO 6
<211> LENGTH: 457
<212> TYPE: PRT
<213> ORGANISM: Trichoderma reesei
<220> FEATURE:
<223> OTHER INFORMATION: Exo-rhamnogalacturonase (rgx 1)

<400> SEQUENCE: 6

```
Met Val Ala Leu Ser Ser Ile Ile Leu Ala Ala Leu Pro Ile Ala Leu
1               5                   10                  15

Ala Val Ser Ser Ser Ala Pro Asp Leu Met Gly Arg Glu Ala Asn Ala
            20                  25                  30

Ala Gln Thr Glu Ser His Trp Ala Asn His Ala Ala Gln Gly Arg
        35                  40                  45

His Phe Cys Tyr Val Arg Pro Asp Ala Asp Gly Asp Asp Ala Pro
50                  55                  60

Ala Ile Met Asp Ala Leu Asn Asn Lys Cys Asn Ser Arg Ser Leu Val
65                  70                  75                  80

Ile Phe Pro Gly Pro Val Tyr Asn Ile Gln Thr Asn Met Thr Thr Leu
                85                  90                  95

Asn Leu Glu Asp Val Val Ile Tyr Gln Phe Gly Arg Met Leu Trp Ser
            100                 105                 110

Thr Asp Ile Asp Tyr Trp Leu Ser Val Ser Met Pro Val Gly Phe Gln
        115                 120                 125

Asn Gln Ser Thr Val Trp Tyr Phe Gly Gly Asn Asn Val Ile Trp Asp
130                 135                 140

Gly Trp Gly Val Gly Thr Leu Asp Gly Asn Gly Gln Val Trp Tyr Asp
145                 150                 155                 160

Trp Ala Arg Ser Gln Gly Asn Leu Pro His Arg Pro Met Asn Ile Asn
                165                 170                 175

Leu Arg Thr Leu Thr Asn Ser Val Ile Arg Arg Met Arg Phe Val Gln
            180                 185                 190

Ser Gln Met Trp Thr Met Ala Ile Thr Tyr Ser Gln His Val Glu Leu
        195                 200                 205

Asp Asp Ile Tyr Val Asn Ser Thr Ser Ser Gln Trp Ser Thr Leu
210                 215                 220

Asn Thr Asp Gly Cys Asp Thr Ile Phe Ser Asp Ser Ile Thr Phe Arg
225                 230                 235                 240

Arg Trp Thr Val Ser Asn Gly Asp Asp Ala Ile Ala Leu Lys Met Asn
                245                 250                 255

Ser Ser Asn Ile Ala Val Tyr Asp Ser Tyr Phe Glu Asn Gly Gln Gly
            260                 265                 270

Ile Ala Ile Gly Ser Met Gly Gln Tyr Asn Gly Arg Tyr Glu Tyr Leu
        275                 280                 285

Glu Asn Phe Tyr Ala Lys Asn Ile Thr Leu Lys Asn Thr Ala His Val
    290                 295                 300

Ser Tyr Leu Lys Thr Trp Ala Gly Ile Ser Arg Gly Tyr Pro Pro Asn
305                 310                 315                 320

Gly Gly Gly Gly Gly Tyr Gly Val Ala Arg Asn Ile Thr Ile Glu Asp
```

-continued

```
                      325                 330                 335
Val Lys Leu Ile Gly Gly Arg Gln Gln Pro Phe Phe Ala Trp Gln Cys
            340                 345                 350

Glu Asn Tyr Ser Gly Tyr Ala Gly Gln Asp Cys Asp Ser Ser Leu Phe
                355                 360                 365

Lys Met Glu Asp Val Ala Trp Arg Arg Val Ser Gly Thr Val Gln Ser
        370                 375                 380

Gly Val Thr Glu Ala Ala Tyr Phe Gln Cys Ser Ala Ala Ala Gly Gly
385                 390                 395                 400

Cys Asp Asp Phe Glu Val Thr Gly Phe Asp Val Thr Lys Glu Gly Thr
                405                 410                 415

Asp Glu Leu Leu Ala Ile Trp Asp Cys Phe Asn Val Asn Asn Pro Val
            420                 425                 430

Gly Phe Thr Cys Thr Glu Ser Gln Ala Gln Lys Met Ser Ser Asp Val
        435                 440                 445

Thr Gly Gly His Gly Ser Asn Asn Lys
    450                 455

<210> SEQ ID NO 7
<211> LENGTH: 1218
<212> TYPE: DNA
<213> ORGANISM: Trichoderma reesei
<220> FEATURE:
<223> OTHER INFORMATION: Xylogalacturonase (xga 1)
<220> FEATURE:
<221> NAME/KEY: CDS
<222> LOCATION: (1)..(1215)

<400> SEQUENCE: 7 atg ctc ctt ggc ggg tgt ctt gtt ctt gtg gcc gtg gtg gcc aac gtc      48
Met Leu Leu Gly Gly Cys Leu Val Leu Val Ala Val Val Ala Asn Val
1               5                   10                  15 gct gcg gtg aat ttg ctg caa cct ccg acc aag gtc atc aag aga gcc      96
Ala Ala Val Asn Leu Leu Gln Pro Pro Thr Lys Val Ile Lys Arg Ala
                20                  25                  30 tcg acg tgt acg cca gta gcg ggg cgt tca agt gcg aca gat gat aca     144
Ser Thr Cys Thr Pro Val Ala Gly Arg Ser Ser Ala Thr Asp Asp Thr
            35                  40                  45 ctc gcg att caa tcc gcg atc gcc agt tgc tcc tct ggg act att gtt     192
Leu Ala Ile Gln Ser Ala Ile Ala Ser Cys Ser Ser Gly Thr Ile Val
        50                  55                  60 atc cct gcg tct acg act tac cac atc aat acg gcc ctg agc ttc aaa     240
Ile Pro Ala Ser Thr Thr Tyr His Ile Asn Thr Ala Leu Ser Phe Lys
65                  70                  75                  80 ggc tgc tct gga tgc acg ttg caa atc gaa ggc act cta caa gcc ata     288
Gly Cys Ser Gly Cys Thr Leu Gln Ile Glu Gly Thr Leu Gln Ala Ile
                85                  90                  95 tcc gac acc aac tac tgg gaa ggt tta cga gcc atc ttt ctc atg gat     336
Ser Asp Thr Asn Tyr Trp Glu Gly Leu Arg Ala Ile Phe Leu Met Asp
                100                 105                 110 ggc atc aac ggc gcg aac ata tat tca aat acg ggc aaa ggc gtc atc     384
Gly Ile Asn Gly Ala Asn Ile Tyr Ser Asn Thr Gly Lys Gly Val Ile
        115                 120                 125 gat gga aac ggc caa gct gcg tgg gac gtc ttt gca gcc aat tct tcg     432
Asp Gly Asn Gly Gln Ala Ala Trp Asp Val Phe Ala Ala Asn Ser Ser
    130                 135                 140 tat aga cga ccg acg ctc ttc tac atc aac aat tcc aag aac gtc aac     480
Tyr Arg Arg Pro Thr Leu Phe Tyr Ile Asn Asn Ser Lys Asn Val Asn
145                 150                 155                 160 gtc cgt aac ctc tac ttc aag agt gct cca aat gtc ttt cac tcg gtg     528
```

| | | | | | | | | | | | | | | | | |
|---|---|---|---|---|---|---|---|---|---|---|---|---|---|---|---|---|
| Val | Arg | Asn | Leu | Tyr | Phe | Lys | Ser | Ala | Pro | Asn | Val | Phe | His | Ser | Val | |
| | | | | 165 | | | | | 170 | | | | | 175 | | |

```
acc ggc ggc tcc agc aat gtc act tac acc gac atc act ctc tac gcc    576
Thr Gly Gly Ser Ser Asn Val Thr Tyr Thr Asp Ile Thr Leu Tyr Ala
            180                 185                 190 gtg agc aac agc tcc aat gtt gcg cac aac act gac ggc tgg gac atc    624
Val Ser Asn Ser Ser Asn Val Ala His Asn Thr Asp Gly Trp Asp Ile
        195                 200                 205 gga cag tca acc tac gtg agc atc aat cac gcc aca gtc aca aac gac    672
Gly Gln Ser Thr Tyr Val Ser Ile Asn His Ala Thr Val Thr Asn Asp
    210                 215                 220 gat gac tgc gtt gct ttc aag cca ggc agc agc ttc gcg acc gtt acc    720
Asp Asp Cys Val Ala Phe Lys Pro Gly Ser Ser Phe Ala Thr Val Thr
225                 230                 235                 240 aac atc acc tgc aca ggt agc cac ggt atc tcc gtc gga agc ttg ggc    768
Asn Ile Thr Cys Thr Gly Ser His Gly Ile Ser Val Gly Ser Leu Gly
                245                 250                 255 agc ggt gcc gga aat aca gac acg gtt cag aat tgt ttc gtg agc gga    816
Ser Gly Ala Gly Asn Thr Asp Thr Val Gln Asn Cys Phe Val Ser Gly
            260                 265                 270 gcg acc atg att gac tct acc aag gct gca ggt ctc aag ctt tac ccg    864
Ala Thr Met Ile Asp Ser Thr Lys Ala Ala Gly Leu Lys Leu Tyr Pro
        275                 280                 285 ggc ccc ccg aaa cat ggc aca gct atc gtg acc aat gtg act ttt gag    912
Gly Pro Pro Lys His Gly Thr Ala Ile Val Thr Asn Val Thr Phe Glu
    290                 295                 300 aac ttt gtg ttg aag aac acc gac tac gct ttc caa gtt caa agc tgc    960
Asn Phe Val Leu Lys Asn Thr Asp Tyr Ala Phe Gln Val Gln Ser Cys
305                 310                 315                 320 tac ggc gaa gat gca tcg tat tgc agc agc agc ccg agc acc gcg caa   1008
Tyr Gly Glu Asp Ala Ser Tyr Cys Ser Ser Ser Pro Ser Thr Ala Gln
                325                 330                 335 gtc aaa ggc gtg gtg gtg cgg aac ttt tcg ggg acg aca agc agc cat   1056
Val Lys Gly Val Val Val Arg Asn Phe Ser Gly Thr Thr Ser Ser His
            340                 345                 350 tat tcg ccg aat gtt gca aac ctc aac tgc cca gct gct ggg tcg tgc   1104
Tyr Ser Pro Asn Val Ala Asn Leu Asn Cys Pro Ala Ala Gly Ser Cys
        355                 360                 365 ggc ctc acc ttg agc aac atc acg gtg aag ccg ccg agc ggc tca gcc   1152
Gly Leu Thr Leu Ser Asn Ile Thr Val Lys Pro Pro Ser Gly Ser Ala
    370                 375                 380 gtg ttt caa tgt gca aac acg ccc agt agc atc ggg gtg ccg tgc tct   1200
Val Phe Gln Cys Ala Asn Thr Pro Ser Ser Ile Gly Val Pro Cys Ser
385                 390                 395                 400 gct ggc gcc agc gga taa                                           1218
Ala Gly Ala Ser Gly
                405
```

<210> SEQ ID NO 8
<211> LENGTH: 405
<212> TYPE: PRT
<213> ORGANISM: Trichoderma reesei
<220> FEATURE:
<223> OTHER INFORMATION: Xylogalacturonase (xga 1)

<400> SEQUENCE: 8

```
Met Leu Leu Gly Gly Cys Leu Val Leu Val Ala Val Val Ala Asn Val
1               5                   10                  15

Ala Ala Val Asn Leu Leu Gln Pro Pro Thr Lys Val Ile Lys Arg Ala
            20                  25                  30

Ser Thr Cys Thr Pro Val Ala Gly Arg Ser Ser Ala Thr Asp Asp Thr
```

```
                35                  40                  45

Leu Ala Ile Gln Ser Ala Ile Ala Ser Cys Ser Ser Gly Thr Ile Val
 50                  55                  60

Ile Pro Ala Ser Thr Thr Tyr His Ile Asn Thr Ala Leu Ser Phe Lys
 65                  70                  75                  80

Gly Cys Ser Gly Cys Thr Leu Gln Ile Glu Gly Thr Leu Gln Ala Ile
                 85                  90                  95

Ser Asp Thr Asn Tyr Trp Glu Gly Leu Arg Ala Ile Phe Leu Met Asp
                100                 105                 110

Gly Ile Asn Gly Ala Asn Ile Tyr Ser Asn Thr Gly Lys Gly Val Ile
                115                 120                 125

Asp Gly Asn Gly Gln Ala Ala Trp Asp Val Phe Ala Ala Asn Ser Ser
130                 135                 140

Tyr Arg Arg Pro Thr Leu Phe Tyr Ile Asn Asn Ser Lys Asn Val Asn
145                 150                 155                 160

Val Arg Asn Leu Tyr Phe Lys Ser Ala Pro Asn Val Phe His Ser Val
                165                 170                 175

Thr Gly Gly Ser Ser Asn Val Thr Tyr Thr Asp Ile Thr Leu Tyr Ala
                180                 185                 190

Val Ser Asn Ser Ser Asn Val Ala His Asn Thr Asp Gly Trp Asp Ile
                195                 200                 205

Gly Gln Ser Thr Tyr Val Ser Ile Asn His Ala Thr Val Thr Asn Asp
                210                 215                 220

Asp Asp Cys Val Ala Phe Lys Pro Gly Ser Ser Phe Ala Thr Val Thr
225                 230                 235                 240

Asn Ile Thr Cys Thr Gly Ser His Gly Ile Ser Val Gly Ser Leu Gly
                245                 250                 255

Ser Gly Ala Gly Asn Thr Asp Thr Val Gln Asn Cys Phe Val Ser Gly
                260                 265                 270

Ala Thr Met Ile Asp Ser Thr Lys Ala Ala Gly Leu Lys Leu Tyr Pro
                275                 280                 285

Gly Pro Pro Lys His Gly Thr Ala Ile Val Thr Asn Val Thr Phe Glu
290                 295                 300

Asn Phe Val Leu Lys Asn Thr Asp Tyr Ala Phe Gln Val Gln Ser Cys
305                 310                 315                 320

Tyr Gly Glu Asp Ala Ser Tyr Cys Ser Ser Pro Ser Thr Ala Gln
                325                 330                 335

Val Lys Gly Val Val Arg Asn Phe Ser Gly Thr Thr Ser Ser His
                340                 345                 350

Tyr Ser Pro Asn Val Ala Asn Leu Asn Cys Pro Ala Ala Gly Ser Cys
                355                 360                 365

Gly Leu Thr Leu Ser Asn Ile Thr Val Lys Pro Pro Ser Gly Ser Ala
                370                 375                 380

Val Phe Gln Cys Ala Asn Thr Pro Ser Ser Ile Gly Val Pro Cys Ser
385                 390                 395                 400

Ala Gly Ala Ser Gly
                405

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 9
gatcccgcgg caacatgctc aagctatcac                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatcctcgag cattcttcac ggcattctac                                    30

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagtccgcgg ctaagcaaag gagcacg                                       27

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgtaggatcc gtagtagagt ttcattgcat c                                  31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gactccgcgg cgacttccat catgctcctt g                                  31

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gatcaccgcg gatgctttat g                                             21

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```

-continued

```
gtacccgcgg tcgacagaat ggtggcgcta tc                                    32
```

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
gtcaggatcc agagcggtat caagcagtat c                                     31
```